US007335480B2

(12) United States Patent
Koulchin et al.

(10) Patent No.: US 7,335,480 B2
(45) Date of Patent: Feb. 26, 2008

(54) ENRICHED ANTIBODY FOR DETECTING MYCOBACTERIAL INFECTION, METHODS OF USE AND DIAGNOSTIC TEST EMPLOYING SAME

(75) Inventors: Vladimir A. Koulchin, Portland, ME (US); Elena V. Molokova, Portland, ME (US); Jill L. Kerrick, Scarborough, ME (US)

(73) Assignee: Chemogen, Inc., South Portland, ME (US)

( * ) Notice: Subject to any disclaimer, the term of this patent is extended or adjusted under 35 U.S.C. 154(b) by 0 days.

(21) Appl. No.: 11/186,933

(22) Filed: Jul. 20, 2005

(65) Prior Publication Data

US 2006/0127406 A1 Jun. 15, 2006

Related U.S. Application Data

(60) Provisional application No. 60/589,419, filed on Jul. 20, 2004.

(51) Int. Cl.
*G01N 33/53* (2006.01)
*A61K 39/04* (2006.01)

(52) U.S. Cl. .............................. 435/7.1; 435/4; 435/7.2; 435/7.32; 435/7.9; 435/7.92; 424/9.1; 424/9.2; 424/130.1; 424/164.1; 424/168.1; 424/184.1; 424/234.1; 424/248.1

(58) Field of Classification Search ................ 424/9.1, 424/9.2, 130.1, 164.1, 168.1, 184.1, 234.1, 424/248.1; 435/4, 7.1, 7.2, 7.32, 7.9, 7.92
See application file for complete search history.

(56) References Cited

U.S. PATENT DOCUMENTS

| 5,756,327 A | 5/1998 | Sassanfar et al. ........... 435/183 |
| 6,620,785 B2 | 9/2003 | Lambert, Jr. .................. 514/12 |
| 2002/0034763 A1 | 3/2002 | Glatman-Freedman et al. .. 435/7.1 |
| 2002/0103118 A1 | 8/2002 | Lambert, Jr. .................. 514/12 |
| 2004/0038201 A1 | 2/2004 | Nau et al. ....................... 435/5 |

FOREIGN PATENT DOCUMENTS

| WO | WO 92/14155 | 8/1992 |
| WO | WO 97/26007 | 7/1997 |
| WO | WO 97/34149 | 9/1997 |
| WO | WO 01/64237 A1 | 9/2001 |

OTHER PUBLICATIONS

International Search Report; dated Jan. 4, 2006; received Jan. 5, 2006; PCT/US2005/025875.
Anderson, et al. "Specific Immune-Based Diagnosis of Tuberculosis," *The Lancet*, vol. 356, Sep. 2000, pp. 1099-1104.
Apers, et al. "A Comparison of Direct Microscopy, the Concentration Method and the Mycobacteria Growth Indicator Tube for the Examination of Sputum for Acid-Fast Bacilli," *Int. J. Tuberc. Lung*, 2003, pp. 376-381.
Bergmann, et al. "Clinical Evaluation of the Roche AMPLICOR PCR Mycobacterium Tuberculosis Test for Detection of M. Tuberculosis in Respiratory Specimens," *J. Clin Microbiol.*, vol. 34, No. 5, pp. 1083-1085.
Boggian, et al. "Infrequent Detection of Lipoarabinomannan Antibodies in Human Immunodeficiency Virus-Associated Mycobacterial Disease," *J. Clin. Micbiol.*, Swiss HIV Cohort Study., vol. 34, No. 7, pp. 1854-1855.
Britton, W.J., et al. "Separate Antigenic Determinants on Cell Wall Associated Carbohydrate Antigens of Mycobacterium Ieprae Defined with Monoclonal Antibodies" *International Journal of Leprosy and Other Mycobacterial Diseases*, vol. 54, No. 4, Dec. 1986, pp. 545-555.
Burman, et al. "Clinical and Radiographic Features of HIV-related Tuberculosis," *Semin. Respir. Infect.*, vol. 18, No. 4, Dec. 2003, pp. 263-271.
Chan, et al. "Lipoarabinomannan, a Possible Virulence Factor Involved in Persistence of Mycobacterium Tuberculosis Within Macrophages," *Infect. Immun.*, 1991, Vo. 59, No. 5, pp. 1755-1761.
Daffe, et al. "The Envelope Layers of Mycobacteria with Reference to their Pathogenicity," *Adv. Microb. Physiol.*, 1998, vol. 39, pp. 131-203.
Doherty, et al. "Immune Responses to the Mycobacterium Tuberculosis-Specific Antigen ESAT-6 Signal Subclinical Infection Among Contacts of Tuberculosis Patients," *J. Clin Microbiol.*, vol. 40, No. 2, Feb. 2002, pp. 704-706.
Doskeland, et al. "Bacterial Antigen Detection in Body Fluids: Methods for Rapid Antigen Concentration and Reduction of Nonspecific Reactions," *J. Clin. Microbiol.*, 1980, vol. 11, No. 4, pp. 380-384.
Elliot, et al. "Negative Sputum Smear Results in HIV-Positive Patients With Pulmonary Tuberculosis in Lusaka, Zambia," *Tuber. Lung Dis.*, vol. 74, 1993, pp. 191-194.
Githui, et al. "A Comparison Study on the Reliability of the Fluorescence Microscopy and Ziehl-Neelsen Method in the Diagnosis of Pulmonary Tuberculosis," *East Afr. Med. J.*, May 1993, pp. 263-266.
Hamasur, et al. "Rapid Diagnosis of Tuberculosis by Detection of Mycobacterial Lipoarabinomannan in Urine," *J. Microbiol. Methods*, 2001, vol. 45, pp. 41-52.
Houston, et al. "The Association of Tuberculosis and HIV Infection in Harare, Zimbabwe," *Tuber. Lung Dis.*, vol. 75, 1994, pp. 220-226.
Hunter, et al. "Structure and Antigenicity of the Phosphorylated Lipopolysaccharide Antigens from the Leprosy and Tubercle Bacilli," *J. Biol. Chem.*, 1986, vol. 261, No. 26, pp. 2345-2351.

(Continued)

*Primary Examiner*—Rodney P Swartz
(74) *Attorney, Agent, or Firm*—Bromberg & Sunstein LLP

(57) ABSTRACT

The disclosed technology provides an enriched antibody population, highly specific for an antigen of a surface polysaccharide, from a mycobacterium. In a related embodiment, the antibody is enriched by having been raised in an environment that maintains antigenically active antigen. These antibodies may be used in an immunoreactive environment for detecting the presence of a mycobacterial infection in a sample from a subject.

8 Claims, 11 Drawing Sheets

OTHER PUBLICATIONS

Johnson, et al. "Tuberculin-Purified Protein Derivative-, MPT-64-, and ESAT-6-Stimulated Gamma Interferon Responses in Medical Students Before and After *Mycobacterium bovis* BCG Vaccination and in Patients with Tuberculosis," *Clin. Diagn Lab Immunol*, vol. 6, No. 6, Nov. 1999, pp. 934-937.

Johnson, et al. "Impact of Human Immunodeficiency Virus Type-1 Infection on the Initial Bacteriologic and Radiographic Manifestations of Pulmonary Tuberculosis in Uganda," *Int. J. Tuberc. Lung Dis.*, 1997, pp. 397-404.

Jones, et al. "Relationship of the Manifestations of Tuberculosis to CD4 cell counts in patients with Human Immunodeficiency Virus Infection," *Am. Rev. Respir. Dis.*, vol. 148, 1993, pp. 1292-1297.

Karstaedt, et al. "The Bacteriology of Pulmonary Tuberculosis in a Population with High Human Immunodeficiency Virus Seroprevalance," *Int. J. Tuberc. Lung Dis.*, 1998, pp. 312-316.

Kramer, et al. "Delayed Diagnosis of Tuberculosis in Patients with Human Immunodeficiency Virus Infection," *Am. J. Med.*, 1990, vol. 89, pp. 451-456.

Lee, et al. "Mycobacterium Tuberculosis Cell Envelope," *Curr. Top Microbiol. Immunol.*, vol. 215, pp. 1-27.

Levy, et al. "A Reevaluation of Sputum Microscopy and Culture in the Diagnosis of Pulmonary Tuberculosis," *Chest*, Jun. 1989, pp. 1193-1197.

Noordhoek, et al. "A Sensitivity and Specificity of PCR for Detection of Mycobacterium Tuberculosis: Blind Comparison Study Among Seven Laboratories," *Clin. Microbiol.*, 1994, vol. 32, No. 2, pp. 277-284.

Ong, et al.1 "A Molecular Epidemiological Assessment of Extrapulmonary Tuberculosis in San Francisco," *Clin. Infect. Dis.*, 2004, vol. 38, pp. 25-31.

Pereira, et al. "Development of Antigen Detection Assay for Diagnosis of Tuberculosis Using Sputum Samples," *J.Clin. Microbiol.*, vol. 38, No. 6, Jun. 2000, pp. 2278-2283.

Pollock, et al. "Specific Delayed-Type Hypersensitivity Responses to ESAT-6 Identify Tuberculosis-Infected Cattle," *J. Clin. Microbiol.*, vol. 41, No. 5, May 2003, pp. 1856-1860.

Pottumarthy, et al. "A Comparison of Seven Tests for Serological Diagnosis of Tuberculosis," *J. Clin. Microbiol.*, vol. 38, No. 6, Jun. 2000, pp. 2227-2231.

Rajalahti, et al. "Detection of Mycobacterium Tuberculosis Complex in Sputum Specimens by the Automated Roche Cobas Amplicor Mycobacterium Tuberculosis Test," *J. Clin Microbiol.*, vol. 36, No. 4, Apr. 1998, pp. 975-978.

Range, et al. "Trend in HIV Prevalence Among Tuberculosis Patients in Tanzania," *Int. J. Tuberc. Lung Dis.*, 2001, pp. 405-412.

Ratanasuwan, et al. "Evaluation of the MycoDot Test for the Diagnosis of Tuberculosis in HIV Seropositive and Seronegative Patients," *Int. J. Tuberc. Lung Dis.*, 1997, pp. 259-264.

Ravn, et al. "Human T Cell Responses to the ESAT-6 Antigen from Mycobacterium Tuberculosis," *J. Infect. Dis.*, 1999, vol. 179, pp. 637-645.

Sada, et al. "Detection of Lipoarabinomannan as a Diagnosis Test for Tuberculosis," *J. Clin Microbiol.*, 1992, vol. 30, No. 9, pp. 2415-2418.

Sada, et al. "Evaluation of Lipoarabinomannan for the Serological Diagnosis of Tuberculosis," *J. Clin. Microbiol.*, 1990, vol. 28, No. 12, pp. 2587-2590.

Samb, et al. "Risk Factors for Negative Sputum Acid-Fast Bacilli Smears in Pulmonary Tuberculosis: Results from Dakar, Senegal, a City with Low HIV Seroprevalence." *Int. J. Tuberc. Lung Dis.*, 1999, pp. 330-336.

Schwebach, J.R., et al. "Expression of Mycobacterium Tuberculosis Arabinomannan Antigen in Vitro and In Vivo," *Infection and Immunity*, Sep. 2001, vol. 69, No. 9, pp. 5671-5678.

Swaminathan, et al. "Risk of Development of Tuberculosis in HIV-Infected Patients," *Int. J. Tuberc. Lung*, 2000, pp. 839-844.

Tessema, et al. "Clinical and Radiological Features in Relation in Urinary Excretion of Lipoarabinomanna in Ethiopian Tuberculosis Patients," *Scand. J. Infect Dis.*, 2002, vol. 34, pp. 167-171.

Tessema, et al. "Circulating Antibodies to Lipoarabinomannan in Relation to Sputum Microscopy, Clinical Features and Urinary Anti-Lipoarabinomannan Detection in Pulmonary Tuberculosis," *Scan. J. Infect. Dis.*, 2002, vol. 34, pp. 97-103.

Tessema, et al. "Diagnosis Evaluation of Urinary Lipoarabinomannan at an Ethiopian Tuberculosis Center," *Scan. J. Infect. Dis.*, 2001, vol. 33, pp. 279-284.

Ulrichs, et al. "Differential T Cell Responses to Mycobacterium Tuberculosis ESAT6 in Tuberculosis Patients and Healthy Donors," *Eur. J. Immunol.*, vol. 28, 1998, pp. 3949-5958.

Yang, et al. "Identification of Risk Factors for Extrapulmonary Tuberculosis," *Clin. Infect. Dis.*, 2004, vol. 38, pp. 199-205.

ENRICHED ANTIBODY FOR DETECTING MYCOBACTERIAL INFECTION, METHODS OF USE AND DIAGNOSTIC TEST EMPLOYING SAME

CROSS REFERENCE TO RELATED APPLICATIONS

The present application claims priority from provisional patent application U.S. Application Ser. No. 60/589,419, filed Jul. 20, 2004, which is hereby incorporated by reference herein.

TECHNICAL FIELD

The present invention relates to diagnostic tests for detecting microbial-based diseases and conditions, and more particularly for diagnostic tests and methods for detecting tuberculosis.

BACKGROUND

During the last decades TB has evolved from a predominantly pulmonary infection into a multifaceted pathology with a growing rate of extrapulmonary cases. Until to date effective TB prevention programs are hampered by the absence of a rapid and field adapted screening assay. In high-income countries mycobacterial culture remains the diagnostic standard, but it is time-consuming and relatively expensive. Ideally, sputum microscopy based on three sputum smears can identify up to 67% of culture positive cases. HIV co-infection has been reported to impair the demonstration of *Mycobacterium tuberculosis* in sputa, although some investigators do not report any influence of the HIV serostatus on the AFB diagnosis. The higher percentage of extrapulmonary TB in HIV positive TB patients additionally increases the rate of AFB-negative TB cases. This renders tuberculosis an increasing diagnostic challenge and underlines an urgent need for improved laboratory tools for its diagnosis.

Current approaches for diagnosing TB are not satisfactory. The sputum test for pulmonary TB is not always effective, particularly if there are no detectable bacteria in the sputum, or no sputum sample can be obtained. In addition, this diagnostic test requires microscopy and/or culture of the bacteria to confirm the diagnosis, neither of which is especially suitable to diagnosis in the field. cerebrospinal fluid for diagnosis of TB-meningitis is also problematic, particularly in the field since, once again, microscopy and/or culture of the bacteria and/or an ELISA test is usually required to confirm the diagnosis.

Blood tests for TB are also known, but have a poor track record, being complex and unreliable. Urine tests are simpler and more reliable, but current methods require processing of the urine before performing the diagnostic test—such processing usually involving concentration of the urine.

Among the newly developed methods antibody tests against a number of mycobacterial antigens have been developed, but none of these tests has so far reached the needed specificity for routine diagnostic purpose. The drop of sensitivity in HIV positive cases is also a major constraint. A different approach is to measure immune responses to *Mycobacterium tuberculosis* specific antigens like ESAT-6, but so far the differentiation between latent TB infection and TB disease is not possible.

Tuberculosis is an extremely complex pathology existing in multiple forms, but always starting as an airborne infection. Pulmonary tuberculosis occurs immediately at the entry point of the microorganism and extrapulmonary tuberculosis is the result of further penetration into the body of the patient with the most widespread examples of tuberculous meningitis and bone tuberculosis. Complexity of the pathology determines multitude of various approaches tried during this century of modern medicine. Furthermore clinical and radiographic manifestations of HIV-related pulmonary tuberculosis are dramatically altered by immunodeficiency. These factors severely limit our capability of early symptomatic recognition of tuberculosis in HIV/TB patients and also increase the danger of TB transmission to relatives and caregivers of such patients.

Mycobacteria can potentially be recovered from a variety of clinical specimens, including upper respiratory collections (sputum, bronchial washes, bronchoalveolar lavage, bronchial biopsies and such); urine, feces, blood, cerebrospinal fluid (CSF), tissue biopsies, and deep needle aspirations of virtually any tissue or organ. Bacterial culture remains the gold standard in the diagnosis of tuberculosis, but it can take up to 6-8 weeks to make a conclusive diagnosis. There are three major technologies used for rapid (faster than bacterial culture) diagnosis of the mycobacterial infections:

Direct microscopy of sputum smears;
PCR-based assays;
Immunodiagnostic methods.

Direct microscopy of sputum smears. More than a century ago, Robert Koch identified the etiologic agent of tuberculosis by staining it and culturing it from clinical specimens. Today, the diagnosis of tuberculosis is usually established using staining and culturing techniques that do not differ substantially from those that Koch used. Direct microscopy of sputum is the norm for the diagnosis of tuberculosis in developing countries today and it is the benchmark against which the efficiency of any new test must be assessed. It is applied to pulmonary tuberculosis, but is not very useful for children or for patients with initial stages of pulmonary tuberculosis.

PCR-based assays. A comparative study of the performance of PCR tests in seven laboratories has shown high levels of false-positive PCR-results, ranging from 3% to 20% (with an extreme of 77% in one laboratory). This relatively poor performance resulted from lack of monitoring of each step of the procedure and underscores the necessity for careful quality control during all stages of the assay.

Immunodiagnostic Methods.

The Tuberculosis Skin Test. This is the probably oldest immunological test for tuberculosis. A small amount of substance called PPD Tuberculin is placed just under the top layer of the skin on the forearm with a small needle. The test is read 48 to 72 hours after it has been given. Generally, a swelling of 10 mm. or more is considered positive. Many developing countries use BCG vaccination to protect against TB. After BCG vaccination, the PPD skin test usually becomes positive. Results of the skin test vary dependent on the quality of the PPD antigen, reactivity of the immune system and probably even race of the individual. This test also does not provide an unequivocal indication about the stage and location of the infection.

Serological tests for *M. tuberculosis*. This approach, based on the detection of antibody immune response to mycobacterial antigens is one of the most widely used in research and clinical environments. All serological tests have approximately the same sensitivity and specificity if they use purified antigens. The sensitivity of the best tests is in a range of 80% for smear-positive cases and 60-70% for smear negative cases. The reported specificity is generally high and is in a range of 95-100%.

Currently existing technologies are limited in their performance in several ways.

Most widely accepted rapid microscopic test requires several hours to complete, skillful technician and clinical laboratory environment. Test interpretation is far too difficult compared to current standards of rapid POC (point of care) testing in the infectious diseases area. Real cost of one analysis per one patient runs in the range of $100-150 for a US hospital. Clinical specificity of the test is very good, but any improvements in sensitivity will be more than welcome.

Skin test has sufficient sensitivity, but takes a long time and does not provide information about stage of pathological process and does not sufficiently differentiate infected and vaccinated individuals.

Serological tests usually do not have sufficient sensitivity. Test results vary with variations in the individual immune response to TB antigens. These tests practically do not work in HIV patients infected by *M. tuberculosis*. This factor severely limits their applicability in Africa and many Asian countries. In the US this group of patients constitutes the majority of TB infected patients as well.

PCR tests are widely used in developed countries, but are complex, expensive and are not sensitive enough to justify their use as a screening test in developing countries.

A preferred method for rapid diagnosis of infectious diseases is based on the detection of a bacterial antigen in the patient sample, that provides unequivocal proof of active infectious process caused by specific pathogen. The concept of using a direct antigen test for detection of mycobacterial infections was described in several publications.

For example, the development of one of the first direct antigen assay for *M. tuberculosis* was reported in 1982—a radioimmunoassay for the detection *M. tuberculosis* antigens in sputum of patients with active pulmonary tuberculosis, using a rabbit antibody specific to the whole cells of *M. bovis* (BCG vaccine). Autoclaved and sonicated sputum was used as a sample. The assay detected antigen in 38 of 39 sputum samples from patients with active tuberculosis pulmonary tuberculosis.

Later studies reported the development of the ELISA system for the detection of mycobacterial antigens in the cerebrospinal fluid of patients with tuberculous meningitis, also using antibodies specific to the whole cells of *M. bovis*. Both systems showed surprisingly high specificity. Despite the fact that LAM was the major antigen responsible for the detection, it was reported that *M. kansasii* showed 5% cross-reactivity, and *M. intracellulare, M. avium, M. fortitum*, and *M. vaccae* cross-reacted only at 2%. Others reported detection, by ELISA, of mycobacterial antigen in the CSF of nine of 12 patients with tuberculous meningitis, corresponding to the sensitivity of 81.25%. Specificity of the test was equal to 95%.

Practically all previous attempts to develop a test for diagnosis of tuberculosis have focused on the detection of the pulmonary form of the disease. Extrapulmonary forms, which are notoriously difficult to diagnose, attracted relatively little attention due to low prevalence rate compared to pulmonary forms. Until the 1950s and 1960s, extrapulmonary TB cases comprised only around 10% of all tuberculosis cases. The onset of the HIV/AIDS pandemic has changed the situation completely. These two diseases eventually merged into a new complex public health problem. Now fully 60% of untreated HIV patients develop active TB during their lifetime and up to 70% of TB patients are HIV infected in sub-Saharan Africa and Asia. Superimposition of HIV and TB changed not only the epidemiology of tuberculosis, but also the course of the disease itself. During the last decades TB has evolved from predominantly a pulmonary infection into a multifaceted pathology with an ever growing prevalence of extrapulmonary forms. It is estimated that extrapulmonary TB cases currently comprise up to 30% of all cases of tuberculosis; this number might even be an underestimation due to the lack of tools for rapid screening and diagnosis of extrapulmonary forms of tuberculosis. Moreover, even pulmonary tuberculosis in HIV patients frequently exhibits atypical symptoms. For example, such patients typically do not produce sputum. These factors severely limit our capability of early symptomatic recognition of tuberculosis in HIV/TB patients and also increase the danger of TB transmission to relatives and caregivers of such patients. An easy to use screening test, capable of detecting a broad spectrum of pathologies due to *M. tuberculosis* infection, is urgently needed, including a test for extrapulmonary forms of TB. Such a need has long been discussed with no progress towards realising goal. Today the need has became a public health care emergency.

In other cases of pulmonary bacterial infections, the current screening process of choice is based on the detection of polysaccharide antigens secreted in the patient's urine. Bacterial polysaccharides are composed of monosaccharides uncommon to humans and therefore resistant to cleavage by human enzymes. This enables their secretion in urine in immunochemically intact forms suitable for detection by a polysaccharide-specific immunoassay. Extremely low concentrations of bacterial polysaccharides secreted in urine require very high sensitivity of the immunoassay in order to use it as a screening procedure.

Collaborating research groups from Sweden and Norway attempted development of a LAM-specific ELISA system detecting LAM antigen in patient urine. The system used antigen capture for detecting tuberculosis from urine based on lipoarabinomannan, a polysaccharide present on the surface of *Mycobacterium tuberculosis*, the organism responsible for causing tuberculosis in humans, as disclosed in PCT application no. WO97/34149 to Svenson, hereby incorporated by reference herein. The disclosed diagnostic procedure detected the presence of LAM in patient urine in 81.3% of AFB-positive patients and 57.4% of AFB-negative patients and demonstrated utility of the detection of mycobacterial LAM antigen for diagnosis of mycobacterial infections. At the same time the system failed to demonstrate utility of the disclosed process for screening purposes. Despite use of the affinity purified rabbit polyclonal antibody specific to LAM antigen, the procedure lacked sufficient sensitivity to be used on non-processed un-concentrated urine samples. The diagnostic procedure required approximately 24-48 hrs of sophisticated manipulations in a biochemical lab focused on concentrating patient urine and preparing it for analysis by ELISA test. Overall, the sensitivity of the Svenson assay is not sufficient for practical use of the disclosed method. The complexity and length of the immunoassay also prevents its practical use as a screening test for detection of mycobacterial infections because it proved too cumbersome for use in a clinical setting, where speed, ease of use, and high sensitivity are all critically important for diagnostic tests used to detect disease conditions.

SUMMARY OF THE INVENTION

In a first embodiment of the invention there is provided an antigenically active iso form of lipoarabinomannan from mycobacterium tuberculosis, prepared by oxidation of LAM using mild oxidation methods such as treatment with low concentrations of NaIO$_4$. In other embodiments, the antigenically active isoform of LAM, generated by mild oxidation methods, is used to prepare highly specific, highly pure antibodies to inactivated mycobacterium, more particularly to surface polysaccharides such as LAM, for use in the detection of polysaccharides (e.g. LAM) in urine, sputum, blood, tissue or other samples from patients of interest. Other embodiments use the highly specific, highly pure antibody raised to the antigenically active form of LAM to diagnose tuberculosis in patients of interest.

In another particular embodiment, there is provided an enriched antibody population highly specific for an antigen of a surface polysaccharide from a mycobacterium. In this embodiment, the enriched antibody population may be enriched by having been raised in an environment that maintains antigenically active antigen. Alternatively or in addition, the antibody is enriched by exclusion of antibodies that recognize relatively inactive antigen. In some embodiments, the mycobacterium may be *Mycobacterium tuberculosis*. Similarly, the surface polysaccharide may be lipoarabinomannan (LAM).

In another embodiment, there is provided a process for producing an enriched antibody highly specific to an antigen of a mycobacterium. In this embodiment, the process comprises raising and isolating antibody to antigen from mycobacteria; and separating from the isolated antibodies that population of antibodies which is specific to relatively inactive antigen to produce isolated enriched antibody.

In another embodiment, there is provided a process for producing an enriched antibody highly specific to an antigen of a mycobacterium. In this embodiment, the process comprises isolating antigen from mycobacteria under conditions maintaining antigenic activity; and raising antibodies to the isolated antigen while maintaining its antigenic activity.

In still another embodiment, there is provided a process for producing an enriched antibody highly specific to an antigen of a mycobacterium. In this embodiment, the process comprises applying sera from a mammal inoculated with mycobacteria to a first affinity matrix prepared with isolated antigen from mycobacterium such that antibody specific to the isolated antigen is retained by the first affinity matrix; isolating antibody specific to the isolated antigen from the first affinity matrix; applying the isolated antibody to a second affinity matrix prepared with modified antigen from mycobacterium such that antibody specific to the modified antigen is retained by the second affinity matrix, wherein the modified antigen has been treated with an agent to deactivate it relative to the isolated antigen; isolating enriched antibody specific to the isolated antigen by collecting effluent from the second affinity matrix, so that the enriched antibody is more highly specific and displays higher sensitivity to mycobacterium antigen than non-enriched antibody.

In further related embodiments, the mycobacterium may be *Mycobacterium tuberculosis*. and the surface polysaccharide may be lipoarabinomannan (LAM).

In other embodiments, the agent for modifying the antigen from mycobacterium is sodium periodate. In other related embodiments, the surface polysaccharide may be isolated from Freund's adjuvant.

Still another embodiment provides a method for detecting a mycobacterial infection in a sample from a subject. In this embodiment, the method comprises providing an immunoreactive environment, such environment developed from the enriched antibody as described above; and reacting the sample in the immunoreactive environment so as to detect the mycobacterial infection.

Optionally the mycobacterial infection may be *M. tuberculosis* or Johne's disease. Similarly, the surface polysaccharide may be lipoarabinomannan (LAM). In further related embodiments, the immunoreactive environment comprises an ELISA, and may be implemented as a strip test. In related embodiments, the mycobacterial infection may be a pulmonary *Mycobacterium tuberculosis* infection or an extra-pulmonary *Mycobacterium tuberculosis* infection, and the sample may be any of sputum, blood, urine, tissue or other suitable sample. In a related particular embodiment, the sample may be non-processed unconcentrated urine.

Other embodiments provide a kit for detecting a mycobacterial infection in a sample, the kit comprising an assay providing an immunoreactive environment wherein the environment comprises an enriched antibody as described above. In related embodiments, the immunoreactive environment comprises an ELISA, and may be implemented as a strip test. In further related embodiments, the mycobacterial infection may be *Mycobacterium tuberculosis* and the surface polysaccharide may be lipoarabinomannan (LAM).

BRIEF DESCRIPTION OF THE DRAWINGS

The foregoing features of the invention will be more readily understood by reference to the following detailed description, taken with reference to the accompanying drawings, in which.

*Klebsiella pneumoniae, Streptococcus agalactiae, Streptococcus pneumoniae* 14/12F, *Pseudomonas aeruginosa, Staphylococcus aureus* 25923/43300, *Proteus vulgaris, E. coli* 8739, *Neisseria meningitidis* A/B/13102, *Haemophilus influenzae* A/B/D. Open triangles represent ELISA results for binding of LAM-specific antibodies to antigens of *M. tuberculosis*, whereas the remaining symbols (e.g. solid triangles, open and solid diamonds, open and solid circles.) represent ELISA results using the same LAM-specific antibodies with other bacterial species described above.

Figure 4A:
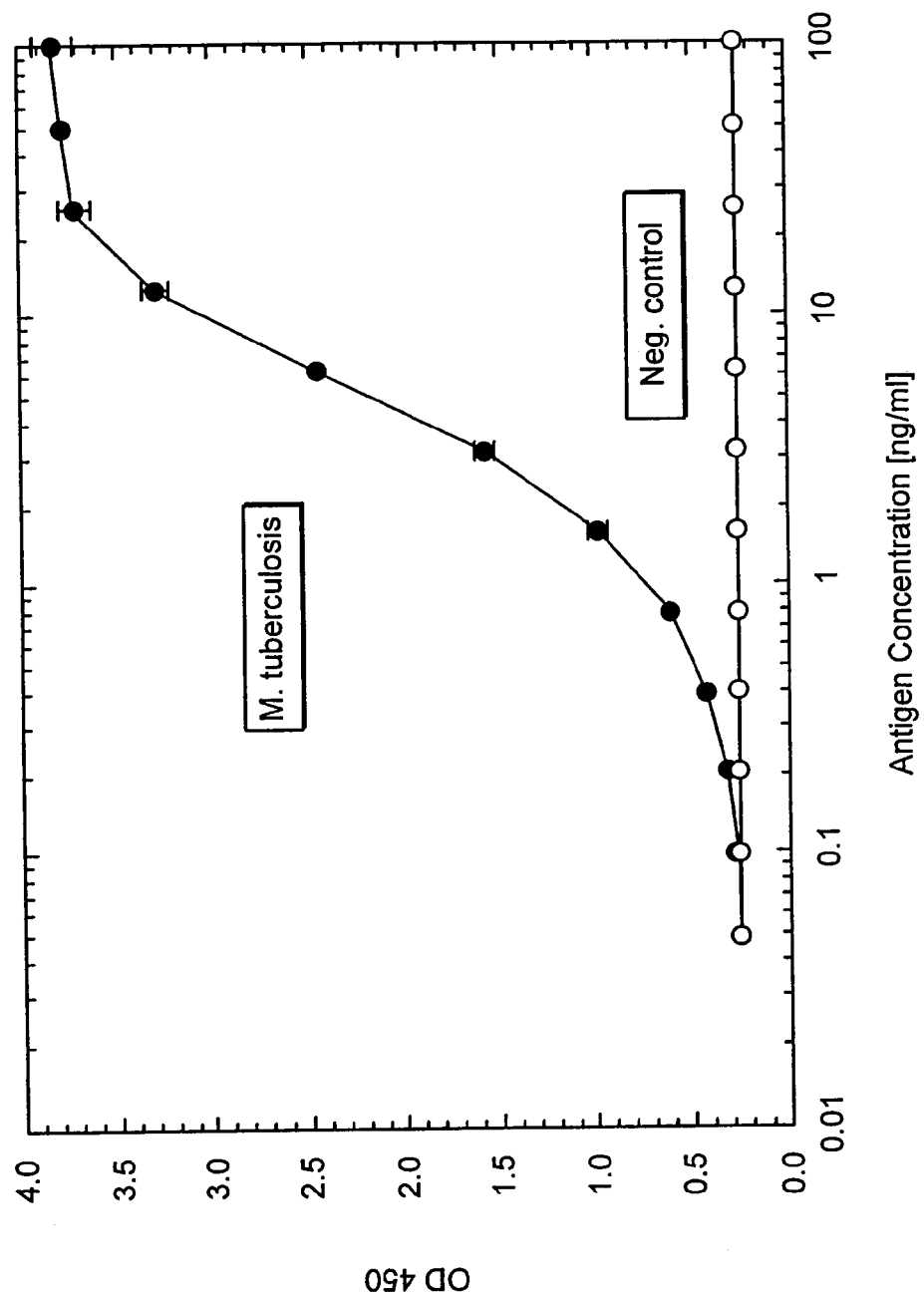
FIG. 4A Sensitivity of the LAM ELISA for different concentrations of LAM in urine. Solid circles represent ELISA results using LAM from *M. tuberculosis*, and open circles represent the control ELISA results. The cut off was the Optical Density of the Negative Control+0.1, resulting in a minimal detection limit of 0.25 ng/ml.
Figure 4B:
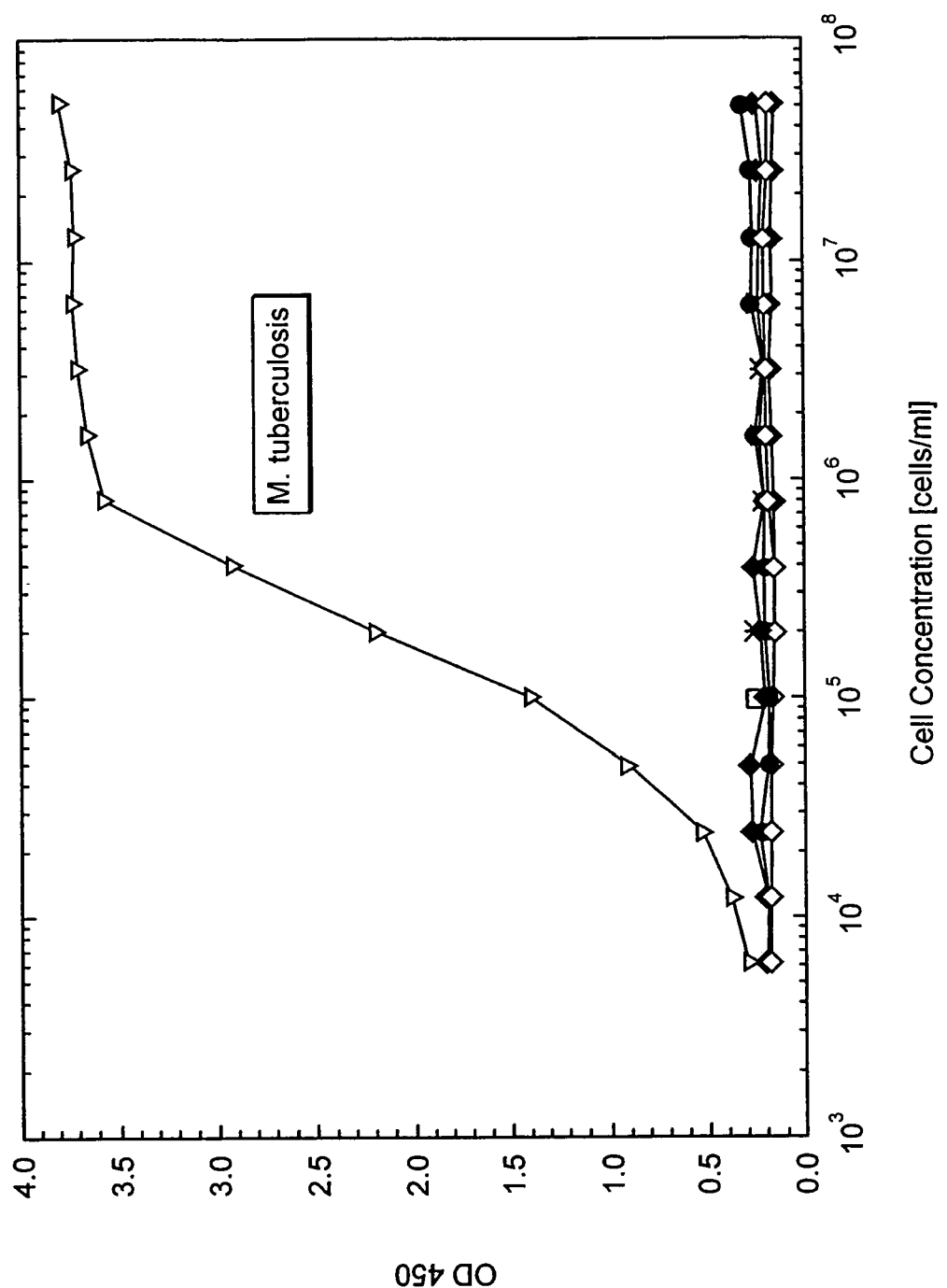
FIG. 4B Binding of LAM-specific antibodies in the ELISA to non-mycobacterial antigens was excluded for the following bacterial species.
Figure 4C:
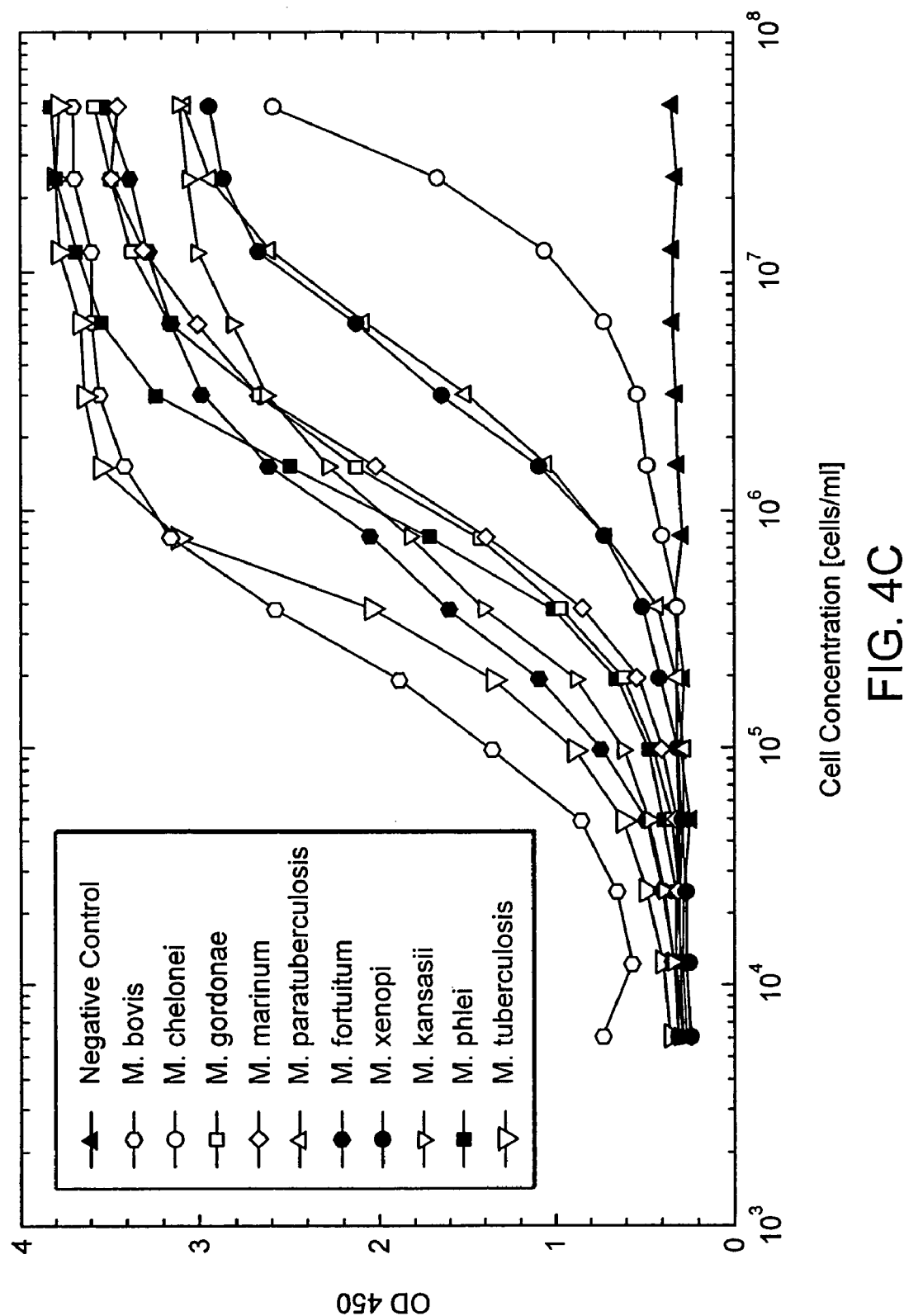

FIG. 4C Sensitivity of the LAM ELISA for various mycobacterial strains. LAM of *M. bovis* and *M. tuberculosis* are detected most sensitively.

Figure 5:
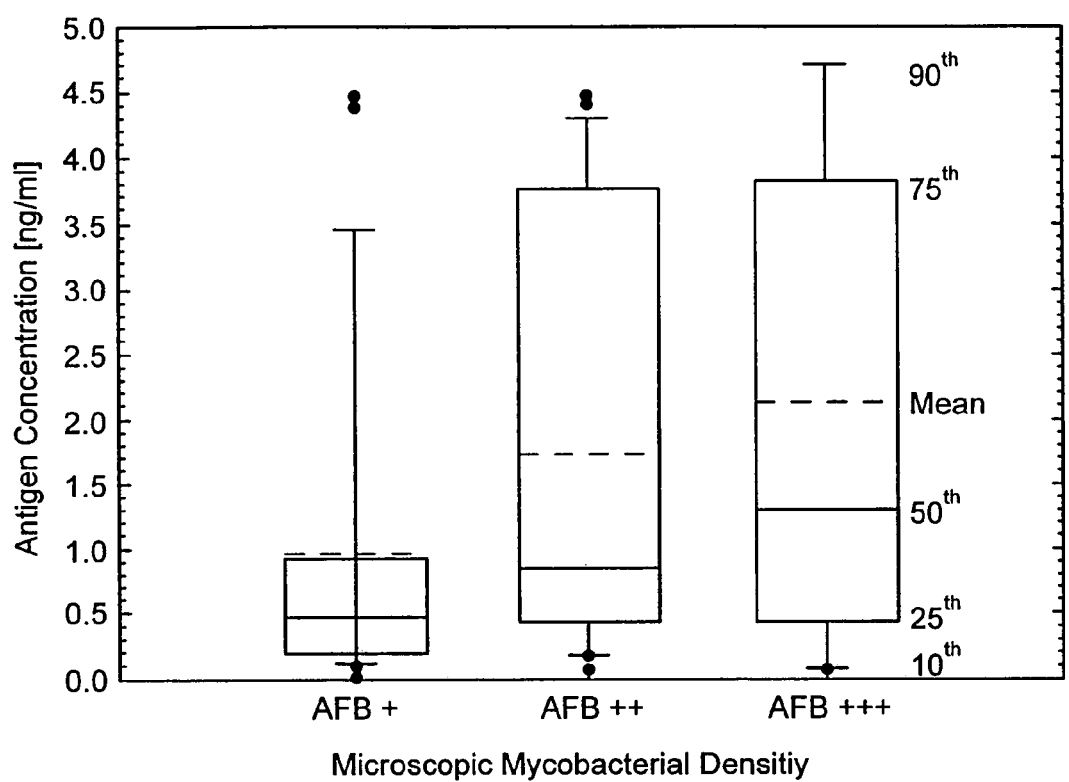

FIG. 5 Correlation between the microscopic mycobacterial density of AFB positive patients and their antigen concentration measured by the LAM ELISA in unprocessed urine. AFB+(light microscopy 1000× magnification: 4-90 acid fast bacilli/100 fields) 28 cases. AFB++(1-9/field) 23 cases. AFB+++(~10/field) 20 cases. Box plot showing $10^{th}$, $25^{th}$, $50^{th}$, $75^{th}$, $90^{th}$ percentile and the mean antigen concentration.

Figure 6:
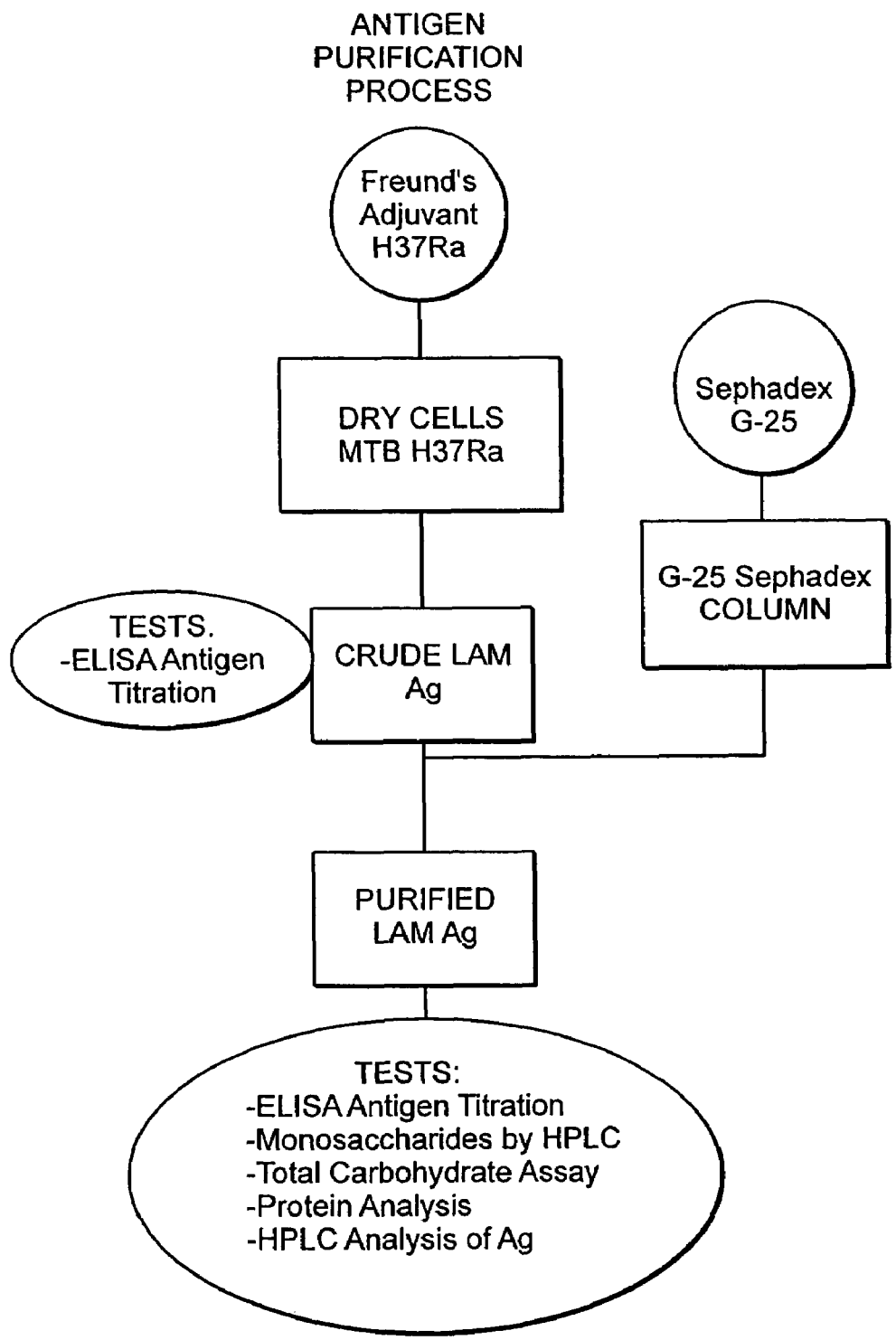

FIG. 6 shows a schematic of an antigen purification process in accordance with particular embodiments of the claimed invention.

Figure 7:
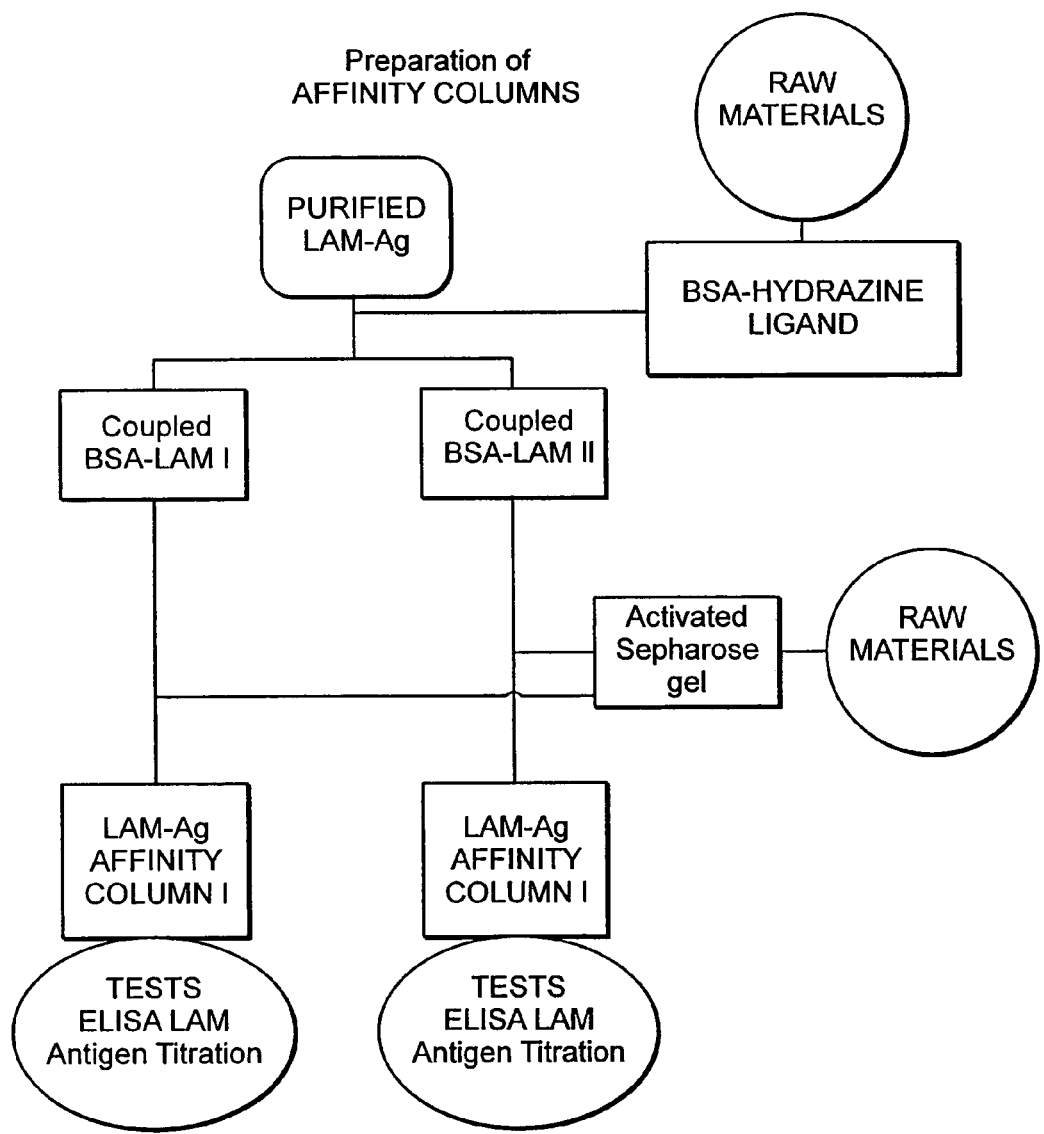

FIG. 7 shows a schematic for preparing affinity columns in accordance with particular embodiments of the claimed invention.

Figure 8:
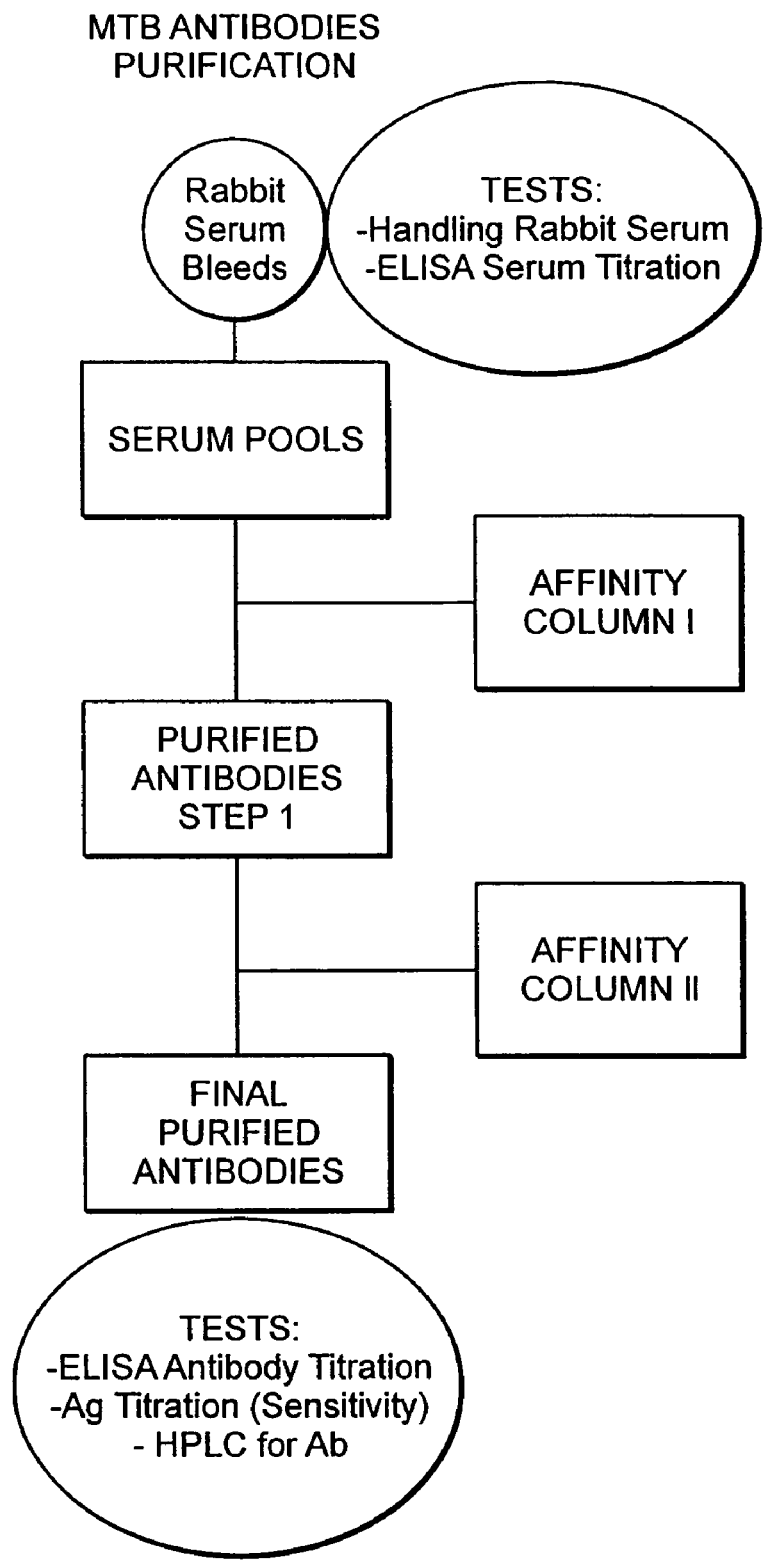

FIG. 8 shows a schematic of an antibody purification process in accordance with particular embodiments of the present invention.

Figure 9:
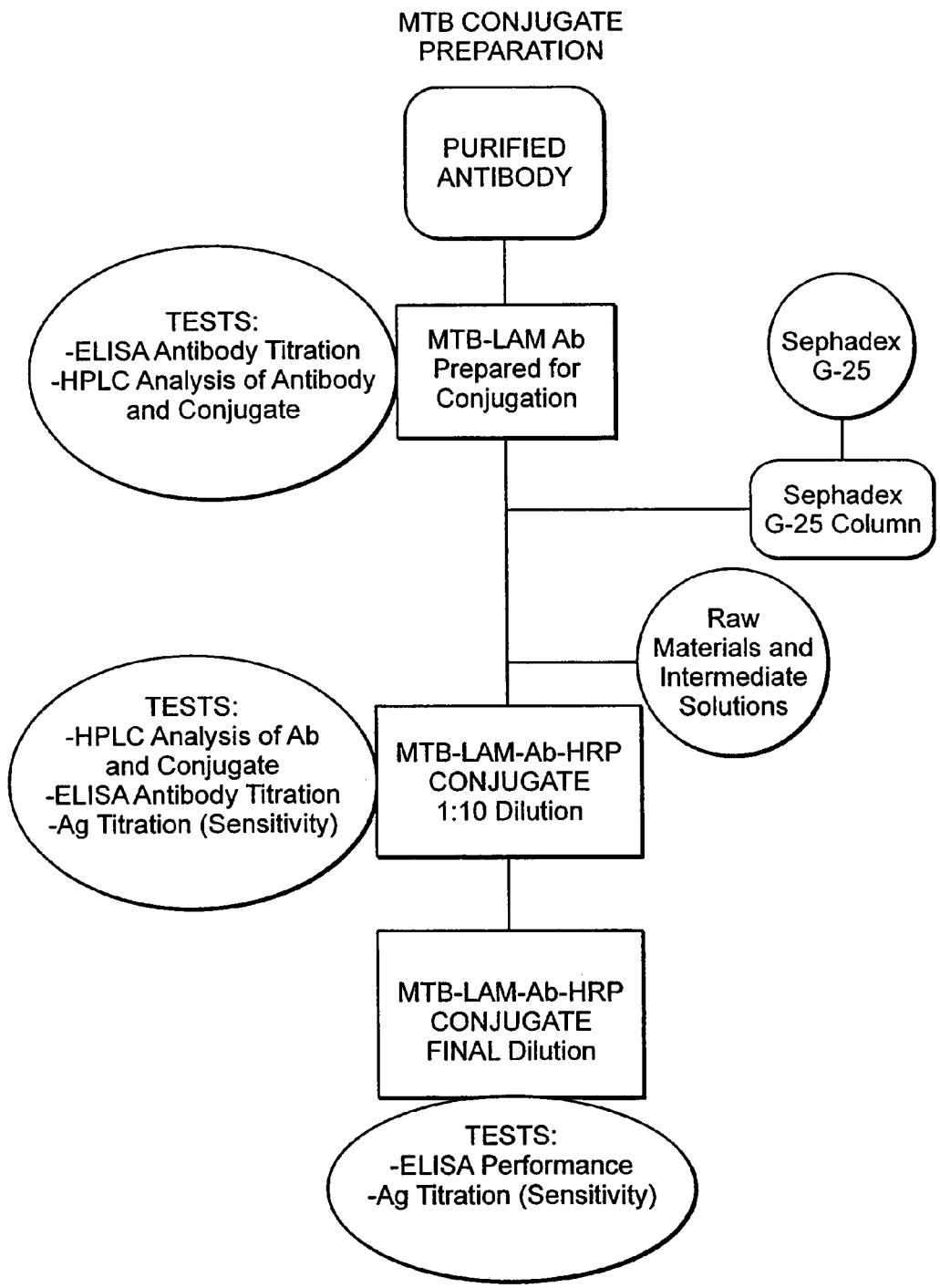

FIG. 9 shows a schematic of a conjugate preparation, in accordance with particular embodiments of the present invention.

DETAILED DESCRIPTION OF SPECIFIC EMBODIMENTS

Definitions

The following terms shall have the meanings indicated unless the context otherwise requires:

"Immunoreactive environment" as used herein means, an environment supportive of immunoassays, immunoreactions, immunochemistry, and any process, assay, methodology or system which involves, relates to or relies on an immunological reaction to achieve a desired result. Examples of immunoreactive environments are those detailed in U.S. Pat. No. 5,073,484 to Swanson et al.; and U.S. Pat. Nos. 5,654,162 and 6,020,147 to Guire et al, incorporated by reference herein, disclosing method and apparatus for quantitatively determining an analyte in a liquid, wherein particular embodiments employ immunochemical reactions in which the analyte and the reactant represent different parts of a specific ligand (antigen)-antibody (anti-ligand) binding pair. These patents relate to technology that has been implemented as what we call in this description and the following claims as a "strip test."

"Freund's adjuvant" is from Sigma, USA.

We have developed a high-sensitivity method for detecting the presence of mycobacterium antigens, particularly *M. tuberculosis* antigens, such as the surface polysaccharides lipoarabinomannan (LAM) and related species, in bodily fluids including but not limited to urine. Heretofore, tests of this nature lacked sensitivity and were not operable for unprocessed urine samples or for detecting extrapulmonary TB infections. In particular, we have developed enriched antibodies raised to antigen from mycobacteria wherein the antibody is enriched by having been raised in an environment that maintains antigenically active antigen. We call the method for producing this first class of enriched antibody the "direct method," which is described in further detail below.

We have also developed antibody that is enriched by exclusion of antibodies that recognize relatively inactive antigen. The method for producing this class of antibodies begins by following the "direct method" to obtain enriched antibodies, but then also operates by excluding antibodies that recognize relatively inactive antigen. We call the method for producing this second class of enriched antibody the "enhanced method," which is also described in further detail below.

FIG. 8 is a schematic depiction showing the steps involved in practicing an embodiment of the enhanced method. Because the enhanced method builds on the direct method, FIG. 8 also illustrates the direct method, if one stops after the first affinity column.

Below we show how these enriched antibodies of either or both classes can be used to detect pulmonary and extrapulmonary infections of TB in a variety of samples, including but not limited to untreated (i.e. non-concentrated) urine samples. (Other potential sources of sample include sputum, cerebrospinal fluid, blood, tissue, ravages.) In the examples which follow, the enriched antibodies are raised to an epitope of lipoarabinomannan (LAM) in an environment which maintains its antigenic activity.

Prior methods for detecting surface polysaccharides (LAM) using different body fluids such as serum, urine or sputum have been investigated, but have proven problematic. In serum, the detection of LAM seems to be disturbed by immune complex formation. Detection of LAM in sputum is possible only in the samples of the patients with pulmonary TB because extra-pulmonary infections often do not provide sputum containing mycobacterial antigens. Prior studies with urine required extensive sample processing and manipulation, limiting such methodologies in the field. None were effective for diagnosing extra-pulmonary mycobacterial infections such as those on the rise in HIV-positive subjects.

Embodiments of the present invention overcome difficulties in the prior art by providing enriched antibodies that may be used for detecting mycobacterial antigens in a wide range of sample types from a subject. These sample types include sera, blood, sputum, lavages, tissue, and unprocessed, non-concentrated urine, among others.

Figure 1A:
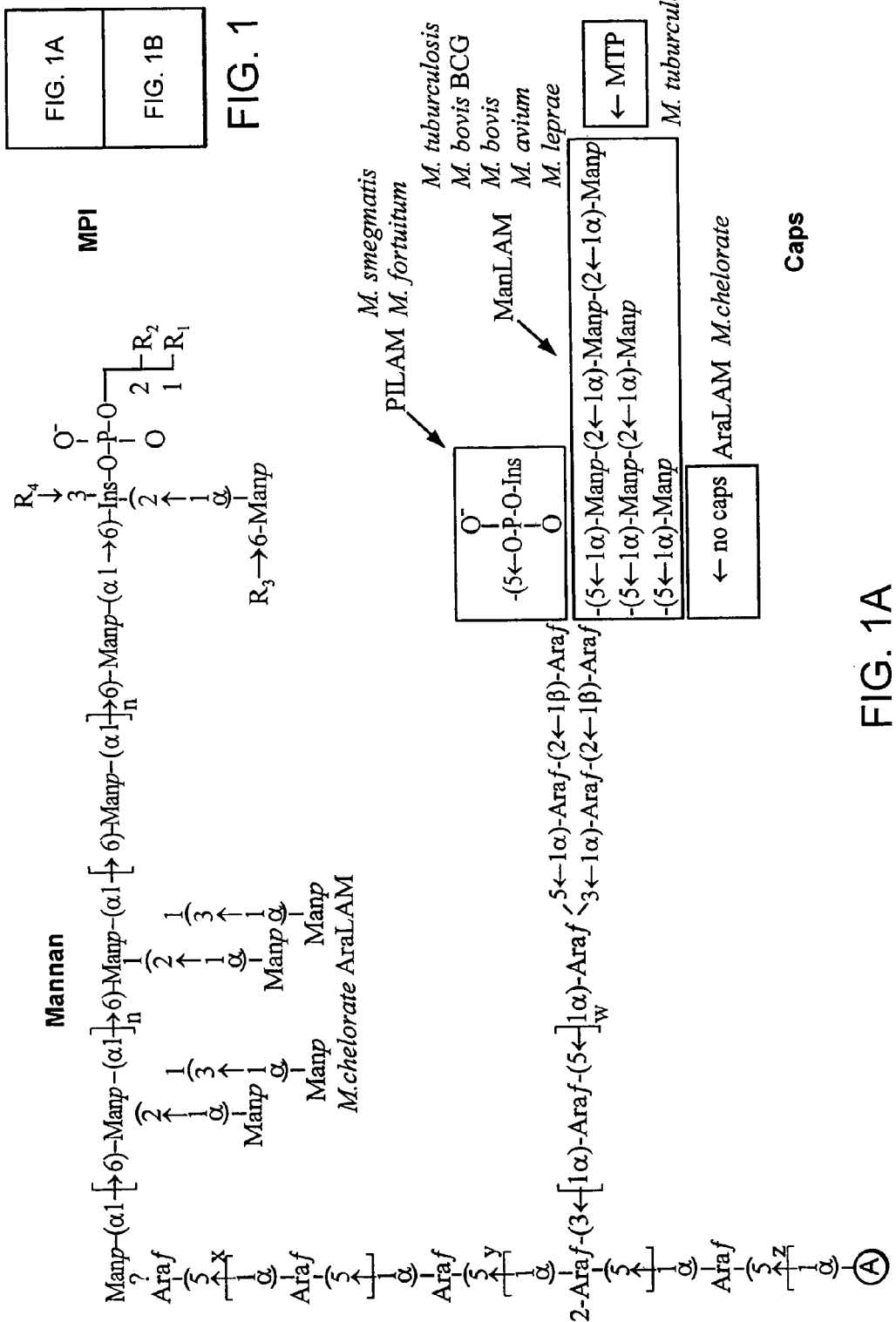
FIG. 1 shows a structural model of mycobacterial Man-LAM, PILAM, and AraLam.
Figure 1B:
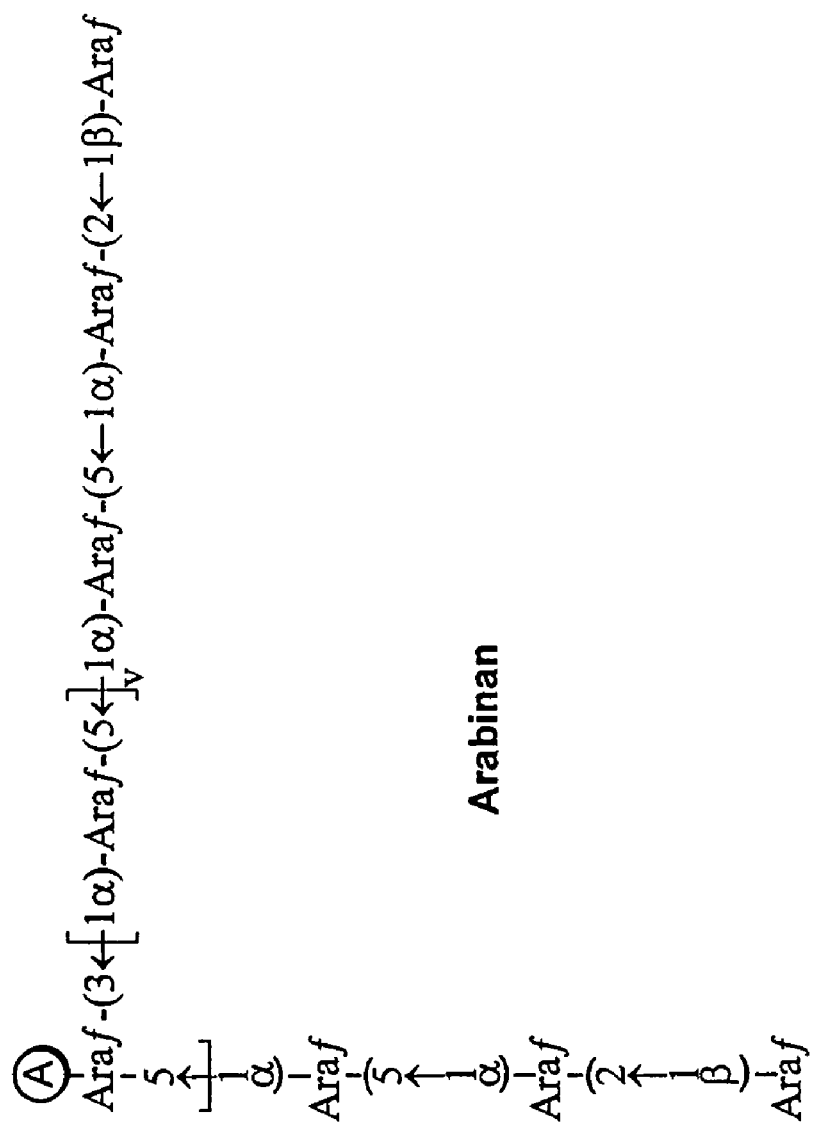

Lipoarabinomannan (LAM) is a 17500 mol wt lipopolysaccharide specific for the genus mycobacterium. Lipoarabinomannan is a complex polysaccharide antigen composed of mannose and arabinose residues forming a highly branched and complex structure. Despite more than four decades of structural studies of polysaccharide antigens of mycobacteria, those in the art still speak only about fragments of the structure or structural motifs and composite models. The most recent composite model of LAM structure is presented in FIG. 1, below.

As part of the outer cell wall of mycobacteria, LAM is released from metabolically active or degenerating bacterial cells. It is assumed that in active TB infection LAM leaks into the circulation, passes through the kidneys and can therefore be detected in the urine reflecting the level of mycobacterial burden. Since LAM is a carbohydrate antigen with glycosidic linkages for which no human degrading glycosidases exist, the antigen occurs in the urine in intact form.

LAM antigen of mycobacteria is composed of three major structural domains: the mannosyl-phospahtidyl-myo-inositol (MIP) anchor, containing variable number of fatty acids with variable chain length; mannan core polysaccharide variable in number of mannose residues; and branched arabinan polysaccharide chains connected to mannan core. Despite many efforts, the attachment site(s) for arabinan chains on the mannan core remain unknown. Arabinan polysaccharide chains are capped by mannose oligosaccharides, consisting of mono-, ($\alpha$1-2)-di- and (al-2)-tri-mannosyl units variable in their length (capping motifs). Capping degree is variable from strain to strain and possibly is also dependent from growth conditions.

Extremely high structural complexity and variability of mycobacterial LAM lead to very complex spectrum of antigenic epitopes. Complexity of the selected diagnostic antigen forces us to use affinity purified polyclonal antibody as a main immunoassay reagent. Only use of polyclonal antibody allows one to cover the full spectrum of antigenic specificities potentially associated with LAM present in clinical samples. In order to achieve the highest possible assay sensitivity of sandwich immunoassay, we use the highest concentration of antigen-specific antibody in the capture zone and also as the labeled antibody. Antigen-specific affinity purification is known to produce such an antibody.

To prepare the antigen-based affinity column, we developed a process for antigen isolation and coupling to the solid phase support. The process of LAM antigen isolation is based, with some minor modifications, on the methods of isolation of other bacterial polysaccharides described in the literature and well-known to those in the art, and described below.

Figure 2:
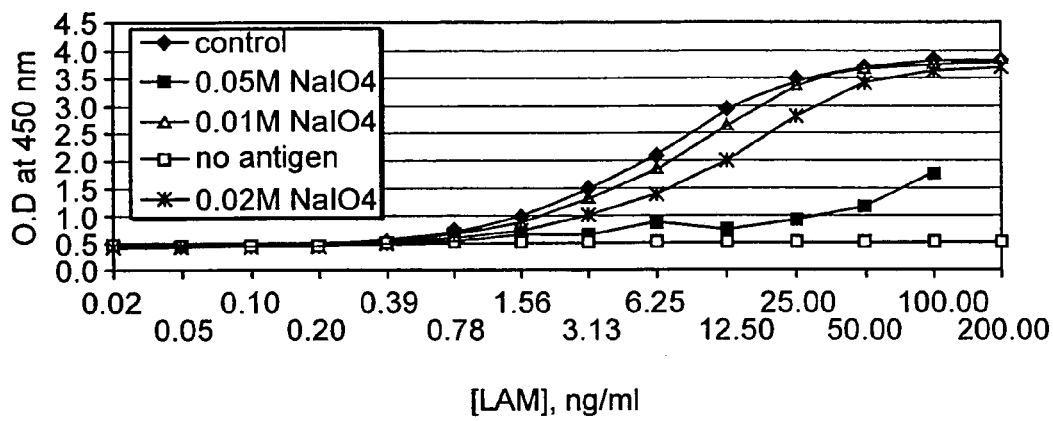
FIG. 2 shows a comparison of serological activity for LAM experiments.

Previous LAM-based direct antigen immunoassay described in the literature used polyclonal antibody purified by antigen-specific affinity chromatography using a LAM-Sepharose column. The prior art approach to the synthesis of the affinity matrix was based on the partial $NaIO_4$-oxidation of LAM polysaccharide with subsequent coupling to $NH_2$-Sepharose. Surprisingly, our experiments have shown that $NaIO_4$-oxidation reduces antigenic activity of LAM polysaccharide, as can be seen from the FIG. 2.

Because coupling efficiency of oxidized polysaccharide to $NH_2$-solid support is proportional to the degree of oxidation, we have coupled to Sepharose support via functionalized BSA-spacer molecule LAM antigen oxidized with 50 mM $NaIO_4$. At this level of oxidation LAM polysaccharide still retains some antigenic activity, as described below, but provides high coupling efficiency. Application of the immune serum to such affinity matrix resulted in the isolation with high yield of the fraction of rabbit antibody. Testing of such antibody in the plate ELISA immunoassay format as a capture antibody showed some functional activity, but not at the level sufficient to be used in the high sensitivity immunoassay necessary for screening applications using non-concentrated urine samples. These data explain results obtained in the literature previously, where LAM-specific affinity purified antibody was used, but it was still necessary to concentrate urine samples in order to detect Lam present in the samples.

Figure 3:
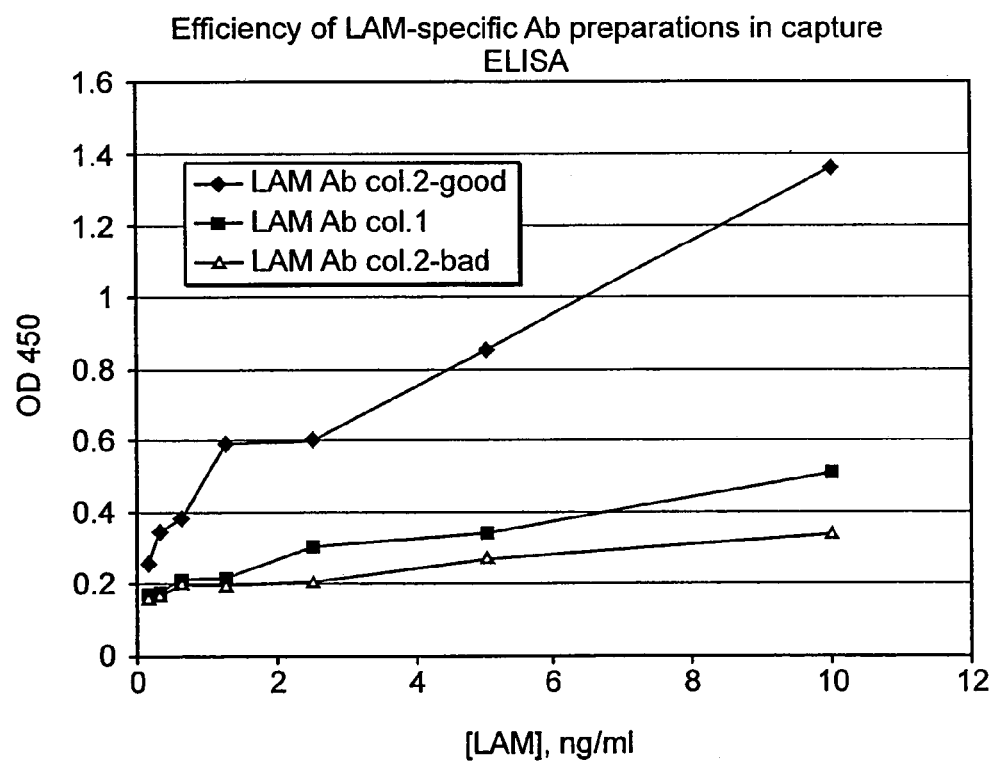
FIG. 3 shows the efficiency of LAM-specific Ab preparations in capture ELISA.

Unexpectedly, by changing the LAM coupling chemistry to a milder non-destructive process, based on polysaccharide activation with cyanogen bromide (CNBr) resulted in the purification of a much better quality of LAM specific antibody, as can be seen in FIG. 3.

Then, surprisingly, passing the antibody purified on the column with intact LAM (CNBr-activation process) through a column with LAM antigen after deep, strong $NaIO_4$ oxidation (see below) produced a relatively small fraction of antibody, approximately 7-10% of the applied amount, with very high activity in the LAM-specific direct antigen immunoassay. FIG. 3 shows the efficiency of such antibody as a capture antibody. When such antibody was labeled with horse radish peroxidase (HRP) and used as a labeling antibody, it also demonstrated activity higher than any other antibody tested or known. The ELISA system based on such antibody has shown extremely high sensitivity and proven to be useful in testing non-concentrated urine samples. This enabled us to produce a screening LAM-specific immunoassay with performance characteristics suitable for rapid screening, in the field, or both pulmonary and extra-pulmonary TB cases, a feat unattainable by others before. Thus, although LAM has been described in the frozen urine of TB patients, the assay for such reports requires an extensive sample preparation and therefore is not field adapted.

Protocols

In this section we describe protocols suitable for practicing the "direct method" and the "enhanced method" defined above. This discussion is not sorted strictly according to the direct method and the enhanced method per se, but describes specifically methods of preparing columns suitable for use in either or both methods, depending upon the context. FIG. 8 shows a schematic of the direct and enhanced methods.

Isolation of Dry Cells of *M. tuberculosis* from Freund's Adjuvant

First, allow cells with Freund's Adjuvant to settle for a minimum of 1 week at room temperature before use. Remove caps from adjuvant vials and without disturbing cells settled on the bottom of the vial, pull off the bulk mineral oil. A small amount of mineral oil may be left in the vial as a precaution to avoid drawing cell precipitate. Discard mineral oil and then mix 6.0 L of ethanol and 6.0 L diethyl ether, and add 5 mL ethanol:diethyl ether mixture to each vial.

Next, close the vial, vortex and quickly transfer the suspension into a 1-L Erlenmyer flask. Avoid letting cells resettle in the vial during this step. When the 1-L Erlenmeyer flask is filled to the 1-L line, let the cells settle for 1-1.5 hr. Next, gently decant solvent from the Erlenmeyer flask into a clean 1-L beaker. Avoid disturbing settled cells and moving them with solvent. If solvent decanted into beaker is clear, discard it. If a significant amount of cells were decanted with the solvent, return the decanted solvent to the Erlenmeyer flask and repeat settling step. Using 20-30 ml aliquots of ethanol: diethyl ether mixture, transfer cells onto a glass sintered filter.

Wash the cells with 500 mL of an ethanol-diethyl ether mixture, then wash with 200 ml of diethyl ether. Next, air-dry cells on a filter using a vacuum of 100 mmHg+/−10 (low vacuum) Occasionally mix and homogenize the cell mass, then cover the filter with a porous material (such as a Kim-wipe) and leave in hood until dry (approximately 15 hours, i.e. overnight).

Weigh and record the total weight and calculate the dry weight of the cells. Then tightly seal with rubber lined cap and store at 15-30° C.

Phenol Extraction of Crude LAM Antigen

Place the dry cells of *M. tuberculosis* into a 250-mL Pyrex media bottle and add warm deionized water to the cells. Vortex and pulse sonicate (~20 second pulses) the suspension in the ultrasonic water bath until suspension is homogeneous.

Phenol extract the cells, then ethanol precipitate and place the precipitated cells in the refrigerator (2-8° C.) overnight (~16 hours) to allow the precipitate to settle. Being very careful not to disturb precipitate, gently draw off the supernatant until about 100 mL of supernatant is left covering the precipitate. Gently swirl to mix, then transfer the remaining suspension into teflon centrifuge tubes and centrifuge at 12,000 rpm for 20 minutes. Draw off as much supernatant as possible from all tubes with out disturbing the pellet, add 5 ml of deionized water to each tube and, using vortexing and pulse sonication, dissolve pellet in water. Combine all the fractions with the dissolved pellet and place in a 500-mL flask (Note: do not exceed 1/10 of the flask capacity/volume). Rotary evaporate to minimal volume, but avoid caramelizing the sample. Redissolve film with approximately 50 mL of water and repeat drying and redissolving until sample has been dried 3 times. Redissolve in 50 mL of water and lyophilize.

Purification of LAM Antigen by Sephadex G-25 Chromatography

Dissolve 800 mg of crude LAM Ag in 15 mL of 0.25% acetic acid solution. Vortex and sonicate in ultrasonic bath to achieve complete dissolution. Centrifuge in a microcentrifuge at 5000 rpm for 5 min. Collect the supernatant in a 20-mL glass vial, divide the supernatant into 3 equal parts for separate chromatographic runs, and then gently apply $\frac{1}{3}^{rd}$ of the LAM Ag supernatant collected above onto the chromatographic column. After a volume of 100 mL has flowed through the column, begin collecting fractions. Continue collecting fractions until 350 mL of mobile phase has passed since the start of chromatography. Cover all fractions and store at 2-8° C. Rotary evaporate in a 250-mL evaporation flask (no volumes greater than 25 mL). Evaporate to minimal volume, but avoid caramelizing the sample. Dilute evaporated material in 20 mL of water, sonicate, vortex until complete dissolution and then lyophilize (approximately 8 hours). Scrape dried material with a spatula into a tared glass vial and weigh.

The foregoing steps are depicted schematically in FIG. 6.

Coupling LAM Antigen to BSA-Spacer by CNBr Activation.

First, prepare 0.5 M sodium bicarbonate and 1 M potassium carbonate solutions. Then dissolve 30.0 mg of purified LAM Ag in 1.5 mL of deionized water. Use pulse sonication (10-20 sec pulses) and vortexing to completely dissolve the LAM Ag.

Dissolve 300 mg of BSA-hydrazine ligand in 15 mL of deionized water. Pulse sonicate (10-20 sec pulses) and vortex to dissolve completely, then place in microfuge tubes and centrifuge in a microcentrifuge for 10 minutes at 10,000 rpm. Using a Pasteur pipette carefully collect and pool the clear supernatant from each tube and transfer into a 20-mL vial. Avoid disturbing any pellet that may form. Add 1.0 mL of 0.5M sodium bicarbonate to the vial and mix well by shaking. Add 150 µL of chilled 1M potassium carbonate to the LAM solution and mix well by brief vortexing. Place obtained solution in ice/water bath.

Prepare 5 mg/mL CNBr in acetonitrile for immediate use and add 180 µL of the cyanogen bromide solution to the LAM solution. Mix by vortexing and place on ice for approx. 15 minutes. Add this solution to the BSA-Hydrazine ligand solution (above) with a Pasteur pipette. Mix well and incubate overnight (16-24 hours), at 2-8° C., in tightly sealed vial.

Coupling of LAM Antigen to BSA-Spacer by $NaIO_4$ Activation

Dissolve the LAM antigen in 1.25 mL of deionized water in a 3-4-mL vial. Pulse sonicate and vortex to dissolve completely. Prepare a 0.1M sodium periodate solution: (in NaOAc buffer, pH 4.0). Add 1.25 mL of the 0.1M $NaIO_4$ solution to the 1.25 mL LAM solution. Vortex to mix. Cover the vial with aluminum foil; place it on the rocking platform and mix for 1 hour+/−5 minutes at ambient temperature.

Dissolve 250 mg of BSA-hydrazine ligand in 12.5 mL of deionized water in a 25-40 mL glass serum vial. Use pulse sonication and vortexing to dissolve completely, then centrifuge for approx. 10 minutes at 10,000 rpm. Using a Pasteur pipette collect the supernatant from each tube and pool into a 25-40 mL glass vial. Avoid disturbing the pellet. Add 12.5 mL of 0.1M sodium phosphate (pH 6.8) to the vial and mix well by brief vortexing.

Coupling Process:

To the BSA-hydrazine solution add the oxidized LAM solution and vortex. Add 100 mg of sodium cyanoborohydride and seal. Sample 10 µL of the final solution and dilute with 90 uL 1×PBS buffer (QC solution) and retain for further analysis (LAM concentration will be approximately 0.75 mg/mL).

Activation of Sepharose by $NaIO_4$

Measure an aliquot of suspension of Sepharose 4B-CL corresponding to 80 ml of settled gel and transfer onto a sintered glass filter. Wash with 500 mL water and drain using low vacuum (approx 300 mmHg) until the granular structure of the gel surface becomes visible. Avoid formation of the air cracks in the gel layer. Prepare a 0.1 M sodium acetate buffer, pH 4.0 solution and use to prepare a 30 mM solution of $NaIO_4$ in 0.1 M NaOAc.

Add 250 mL of 30 mM $NaIO_4$ to the gel and thoroughly mix. Cover the mixture with aluminum foil and place at a 45° angle on a rocker platform at medium speed for 1.5 hours±10 minutes at ambient temperature. Transfer to the sintered glass filter and wash with 1 L of water using low vacuum (approx 300 mmHg). The activated gel must be prepared within a maximum of 4 hours of use.

Coupling of BSA-LAM Ligand to Activated Sepharose (for Synthesis of First and Second Affinity Columns)

Preparation of Matrix

Prepare a 0.1% sodium azide solution in 1×PBS (phosphate buffered saline). Measure a suspension of activated Sepharose corresponding to 60 ml of the settled gel (or other suitable matrix) and transfer it onto a sintered glass filter. Drain gel using low vacuum (300 mm Hg) until the gel packs and granular structure becomes visible, but avoid formation of cracks on the gel surface.

BSA-LAM Ligand Solution:

In a 250-mL media bottle dilute approximately 17 to 20 mL of the solution of BSA-LAM ligand to 90 mL with sodium phosphate buffer (pH 6.8). Add 90 mg of crystalline sodium cyanoborohydride to the solution. Tightly close the bottle using the supplied plastic cap. Mix well by vortexing briefly. The solution may appear opalescent but there should be no precipitate. Microscopic gas bubbles formed by the sodium cyanoborohydride may be visible.

Coupling Step:

To the LAM solution prepared above add the drained activated Sepharose gel. Tightly close and thoroughly mix the suspension using gentle vortexing. Incubate for approx 4 hours at 37° C.+/−2° C., mixing (by inversion) the reaction mixture every hour. Add 4.5 mL of 1.5 M Tris buffer and tightly close cap again. Continue incubating at 37° C.+/−2° C. for approximately 16 hours (overnight).

Transfer the reaction mixture onto a sintered glass filter and collect the liquid phase into a clean 100-200 mL Bunzen flask by applying low vacuum (300 mm Hg). Wash the LAM-Sepharose gel on the filter with 400 ml of deionized water and continue washing with 600 mL of 1×PBS Packing and Storage of Column:

In a 250 mL beaker add 100 mL of 1×PBS to the prepared gel. Stir manually into a slurry. Pack into a column according to standard procedures, using 1×PBS. Equilibrate the column with 1×PBS plus 0.1% sodium azide.

Generic Coupling of LAM Ligand to Activated Sepharose (for Preparation of Affinity Columns I and II)

Measure suspension of Activated Sepharose corresponding to 100 ml of the settled gel and transfer it onto a sintered glass filter. Drain gel using low vacuum (300 mm Hg) until the gel packs and granular structure becomes visible, but avoid formation of cracks on the gel surface. Retain drained gel for later use.

BSA-LAM Ligand Solution:

In 250 mL Pyrex media bottle dilute approx. 27.5 mL solution of BSA-LAM ligand to 100 mL with the sodium phosphate buffer (pH 6.8). Add 100 mg of crystalline sodium cyanoborohydride to the solution. Tightly close the bottle using the supplied plastic cap. Mix well by briefly vortexing. The solution may appear opalescent but there should be no precipitate. Microscopic gas bubbles formed by sodium cyanoborohydride may be visible.

Coupling Step:

To the LAM solution prepared above add the drained activated Sepharose gel. Tightly close with the supplied plastic cap. Thoroughly mix the suspension using gentle vortexing (medium speed) and incubate for approx 4 hours at 37° C.±2° C., mixing the reaction mixture (by inversion) every hour. Add 7.5 mL of 1.5 M Tris buffer and tightly close. Continue incubating at 37° C.±2° C. for approximately 16 hours (overnight).

Transfer the reaction mixture onto a sintered glass filter and collect the liquid phase into a clean 100-200 mL Bunzen flask by applying low vacuum (300 mm Hg). Wash the LAM-Sepharose gel on the filter with approx 800 ml of deionized water. Continue washing with approx 1.2 L of 1×PBS.

Packing and Storage of Column:

In a 250-mL beaker add approximately 160 mL of 1×PBS to the gel above. Stir manually (with spatula/glass rod) into a slurry. Pack into a column according to standard procedures using 1×PBS. Equilibrate the column with 1×PBS with 0.1% sodium azide.

The foregoing steps involving use of purified LAM and preparation of affinity columns I and II are depicted schematically in FIG. 7.

Isolation of Antibody by Affinity Chromatography-I (the "Direct Method").

Prepare the following stock solutions:

1 liter of 0.1M glycine buffer and adjust the pH to 2.5 with 1M HCl.

1 liter of 3×PBS solution (dilute a 10×PBS stock solution with deionized water) and check the pH, and re-adjust to 7.2 to 7.4, if needed, with 1M HCl or 1M NaOH.

200 mL of a 1×PBS plus 0.1% sodium azide solution.

100 mL of a 0.5 M disodium hydrogen phosphate ($Na_2HPO_4$) solution

Serum Preparation

Slow-thaw frozen serum in the refrigerator (approx 16 hours/overnight) until completely thawed. Measure sera volume and weigh 2.9 g of sodium chloride for every 100 mL of serum and add to the sera. Swirl gently until completely dissolved: the final concentration will be 0.5M NaCl.

Centrifuge (4-8° C.) at ~8000 g for 20 minutes. Draw off supernatant from all centrifuge tubes with Pasteur pipette. Do not to disturb the pellet. Filter supernatant through a cotton-plugged funnel and collect the filtrate. Collected filtrate should be slightly opalescent, but should not contain any particulate materials. Place filtered serum in the refrigerator until the beginning of the affinity chromatography step.

Serum Application:

Prepare column I (non-modified LAM coupled to column material) for serum application by equilibrating with 1×PBS. Adjust the flow rate to 2.0 mL/min and continue applying 1×PBS until the baseline remains stable for at least 1 hour. Adjust zero for the recorder and detector as needed. Once the baseline is stable, adjust the flow rate to 0.5 to 0.6 mL/min. and then apply the serum prepared above to the LAM Affinity Column I at the 0.5-0.6 ml/min flow rate. Collect void volume eluant (it will be approximately 30% of the column volume). Monitor fractions by UV detection at 260-280 nm and when an increase in signal occurs, begin collecting serum passed through the column in a 500-1000 mL serum. After the entire volume of serum has been applied to the column, briefly stop the column flow, apply 3×PBS buffer, and then resume liquid flow. Continue to wash column with 3×PBS until the signal decreases to approximately 50% of baseline. At this point stop collection of serum and save all collected fractions. Change the flow rate to 2.0 mL/min and continue washing the column with 3×PBS until baseline is approximately 10-15%. Discard flow-through. Replace 3×PBS buffer with 1×PBS buffer and wash with approx 2-2.5 column volumes at a flow rate of 2.0 mL/min. Discard flow-through.

Elution of Antibodies Step:

Adjust flow rate to 1.0 mL/min. Replace 1×PBS with cold 0.1M Gly-HCl buffer prepared above, and start elution of the adsorbed antibody. When the signal increases rapidly and gains about 10-15% of the full scale, begin collecting eluent column into 15 ml conical tubes placed in ice-water bath (0° C.). Collect 5-ml fractions.

Continue collecting antibodies in Gly-HCl buffer until the signal begins to decrease rapidly. Stop fraction collection when the signal drops to the signal level of the beginning of collection (10-15% of full scale). Neutralize the collected antibody solution by to each 5-mL fraction 0.5 mL of 0.5M $Na_2HPO_4$ in 0.1-ml increments. The total volume added should be equal to 10% of the fraction volume before neutralization.

Gently mix solution during addition of $Na_2HPO_4$ buffer and pool the neutralized fractions. Measure the O.D. of antibodies at 280 nm against a blank containing only 0.1M Gly-HCl buffer and calculate the antibody concentration. Place the antibody collected at 2-8° C. for a minimum of 3 days to allow crashing and shedding.

Column Care:

Equilibrate the column with 1×PBS until neutral (pH 7). During non-use, equilibrate the column with the 1×PBS plus 0.1% sodium azide solution and store the column at 4-8° C. until future use.

Dialysis

Centrifuge prepared antibodies at 10,000 G for a minimum of 5 minutes. Transfer the supernatant to 12-14 mol. wt. cut-off dialysis tubing and dialyze against 1×PBS for 2-3 days with a minimum of 4 changes of buffer, with a ratio of Ab solution to total volume of $\geq$1:20. Remove antibodies from dialysis. Measure volume of antibody solution using glass graduated cylinder. If there is any additional crashing/shedding (in the form of a precipitate) centrifuge the antibody solution again at 10,000 G for a minimum of 5 minutes. Measure the O.D. of antibodies at 280 nm after blanking the spectrophotometer with 1×PBS buffer. Calculate the concentration in mg/mL and place for storage at 4-8° C.

Isolation of Antibody by Affinity Chromatography-II (the "Enhanced Method")

Purification of Highly Specific Antibodies

Apply 1×PBS to the LAM Affinity Column 2 prepared above, (LAM modified by strong oxidation, coupled to column material using $NaIO_4$), at a 2.0 mL/min flow rate until the baseline remains stable for at least 15 minutes. Adjust the recorder and detector to Zero, as required. Continue to monitor the baseline for the next 30 minutes and once stable, apply antibody to the column. Adjust the flow rate to 0.5-0.6 mL/min and apply a volume of antibody, as prepared above, corresponding to ~100-150 mg of Ab to the LAM Affinity Column 2 using an Econo pump or similar device. Collect void volume eluate (It will be approximately 30% of the column volume) at 280 nm. Begin collecting antibodies as the signal increases to about 10-15% above baseline in a clean serum bottle. When the total antibody volume has been applied, briefly stop the liquid flow, apply 1×PBS buffer and resume liquid flow at 0.5-0.6 mL/min. Continue to collect material flowing through column at 280 nm. When the signal drops to 10-15% above the start of collection (30-50% above baseline), stop collecting the solution.

Measure the O.D. of highly specific antibodies at 280 nm after and calculate the antibody concentration. Immediately place antibody solution at 4-8° C. for temporary storage.

Column Wash

Continue to wash the column with 1×PBS at a flow rate of 2.0-2.5 mL/min. Pass minimum 3 column volumes of 1×PBS. Elute material absorbed onto column with cold 0.1M Gly-HCl buffer, prepared above. Collect material eluted in glass vials. When the monitor/signal drops to ~10-15% of baseline, stop collection. Neutralize the collected Antibody solution by adding 10% of total volume of 0.5M sodium phosphate, prepared above, by adding in 0.5 mL increments. Measure the O.D. of antibodies at 280 and calculate the antibody concentration. Immediately place the collected antibodies solution at 4-8° C. and retain until the analysis of antibodies collected in step above is complete. If the concentration of antibodies above is less than 0.3 mg/mL, concentrate.

Wash the column with a minimum of 3 column volumes of 1×PBS at a 2.0-2.5 mL/min flow rate. Wash the column again with 1 column volume of 1×PBS plus 0.1% sodium azide, and store at 4-8° C. until future use.

The foregoing steps showing isolation of enriched antibodies from affinity columns I and II using the direct and enhanced methods are depicted schematically in FIG. 8.

ELISA Plate Coating Process.

Set-Up of the Moduline 300 System.

The Ab coating must be completed within maximum 8 hours from end of preparation of the coating solution M815. The Antibody coating solution must be kept in on ice (0° C.) during the coating process.

Step One

Pre-weigh and inspect empty plates and discard any broken plates. Dispense 100 µl of MTB-LAM specific Ab coating solution into each well of each strip plate using a Moduline 300 System. Visually check all the 96 wells in each plate for uniformity of well filling during coating process. Save unused Ab solution and store at (2-8° C.) until the complete lot of plates are processed and passed for use. Stack plates with dispensed Ab in stacks of 10 plates each and cover the top plate with an empty plate used as a cover. Label each stack cover plate from 1 to 18. Refrigerate the stacked plates at 2-8° C. and incubate overnight (14-18 hrs).

Step Two:

Set-up of the Moduline 300 System to perform 3-times wash cycles followed by immediate dispense cycle of 312 uL Block Solution. Block Solution must be used within maximum 24 hours from end of preparation. Remove plates from refrigerator and remove the covering plates from stacks as they are being placed on the Moduline and place them aside. Set the timer for 6 hours. Set blocked plates coming from the conveyor, on sequentially numbered trays and block for 5 to 6 hours at ambient temperature (20-28° C.).

Place the plates on trays in the Drying Chamber and incubate at 20-23° C. and 20-22% relative humidity for 24-72 hr. Remove dry plates from drying chamber.

MTB-Ab Preparation for Conjugation to HRP (MTB-Ab solution preparation should be performed at least 7 days before conjugation procedure.)

Dialysis:

Dialyze the necessary amount of MTB-LAM-Ab solution against 1×PBS for minimum 48 h with minimum 4 changes, at 2-8° C. Use dialyzing tubing with MWCO 12-14,000. After dialysis centrifuge Ab solution at 12,000 rpm for 10 min. and carefully aspirate supernatant into the 15 ml graduated centrifuge tube.

Measure optical density of Ab solution after dialysis at 280 nm and Calculate Ab concentration after dialysis. If Ab solution after dialysis has $OD_{280\,nm}$>2.8, make a 1:7 dilution of Ab solution in 1×PBS.

Concentration:

Prewash an Amicon Ultrafree-15 centrifugal filter device with 1×PBS. Place approx. 15 mL of 1×PBS solution into device and centrifuge at 3500 rpm for approximately 5 min. Discard all the solution from device units. Concentrate the above Ab solution after dialysis with Ultrafree-15 centrifugal filter devices to 4.5-5.5 mg/ml by centrifugation on Bench-top centrifuge (bucket rotor) at 3500 rpm for approx. 5 min.×3. Carefully aspirate the concentrated Ab solution from the filter unit of the Amicon device into a 15 mL tube. To maximize recovery, remove concentrated sample immediately after centrifugation and resuspend concentrate volume several times with a pipette to ensure proper mixing before Ab aspiration.

Centrifuge the concentrated Ab solution at 10000 rpm for approx. 15 min. and aspirate the Ab supernatant into a 15 mL tube. Measure the $OD_{280}$ of Ab solution at 1:20 dilution in 1×PBS and calculate concentration of Ab.

Sample 0.1 ml of Ab solution for ELISA analysis. Store at 2-8° C.

MTB-LAM-Ab-HRP Conjugate Preparation

Wash all glass vials and stir bars for conjugation steps and glass vials for conjugate storage with $H_2SO_4$ solution and thoroughly rinse them with tap water and deionized $H_2O$.

Preparing the Sephadex G-25 Column for Chromatography:

Obtain a column (1.5×30 cm) with approximately V=50 ml packed with Sephadex G-25 (Fine). Pack the column as described above. Set the following chromatography conditions to equilibrate the column with the 1 mM Sodium Acetate Buffer, pH 4.4.
UV Monitor wavelength for 280 nm
Monitor Sensitivity: 0.2 OD
Chart recorder speed: 2 mm/min.
Pump Flow rate for column washing: 60 ml/h Wash the column with approx 100-150 ml of 1 mM Sodium Acetate, pH 4.4 and adjust the UV monitor baseline to O-position. Make sure that established base line is stable for approx. 30 min. Calculate the amount of MTB-LAM-Ab solution necessary for conjugation and centrifuge Ab at 12,000 rpm for approx. 10 min. Carefully aspirate the Ab supernatant into a clean glass vial. Measure the $OD_{280}$ nm of Ab solution at 1:20 dilution in 1×PBS and Calculate concentration of the undiluted Ab solution. Store the Ab solution at 2-8° C. until use.

Oxidation of HRP (Horse Radish Peroxidase) with $NaIO_4$:

Weigh 8 mg of HRP in V-shaped glass vial. Add 2.0 ml of deionized $H_2O$. Gently stir the solution for approx. 2-3 min. until all the HRP has dissolved. Make sure there are no undissolved HRP particles on the glass vial walls left.

Prepare a fresh solution of 0.1 M $NaIO_4$, pH 4.4 for use within a maximum of 5 minutes and protect from light. Add 0.4 ml of 0.1 M $NaIO_4$ to the HRP solution prepared above, while stirring. Cover the vial with aluminum foil to protect the mixture from light. Incubate the mixture for 20 min. with stirring at ambient temperature. Add 4 drops of ethylene glycol to the reaction mixture and stir for approximately 2 min.

Chromatography and Concentration of Oxidized HRP:

Immediately after completing the above step purify the oxidized HRP by gel-filtration on Sephadex G-25 (Fine) column. Set the pump flow rate for sample elution to approximately 50 ml/h. Carefully apply the total volume of the oxidized HRP prepared above onto the dry gel bed but take care not to disturb the gel bed. Do not over dry gel. Collect all oxidized HRP (colored solution) into one 15 ml tube.—$1^{st}$ peak on the chromatography Chart ($OD_{280\ nm}$> 0.05). After chromatography is completed, empty the column of Sephadex G-25 and discard the gel and record the volume of HRP solution after chromatography.

Concentrating Oxidized HRP

Prewash Ultrafree-15 centrifugal filter devices with 1 mM Sodium Acetate, pH 4.4 with approximately 15 mL of 1 mM Sodium Acetate, pH 4.4, and centrifuge the filter unit for approx. 5 min. at 3500 rpm using a bench-top centrifuge (bucket rotor). Then discard all solutions from the filter unit. Immediately after chromatography, concentrate the oxidized HRP solution (from above) to approx. 2±0.2 ml with an Ultrafree-15 centrifuge filter unit (Biomax-10K membrane) by centrifugation at 3500 rpm for approx. 5 min. Carefully aspirate the concentrated HRP solution from the filter unit of the device into the clean glass vial, measure and record the volume, and store at 2-8° C.

Conjugation HRP to MTB-LAM-Ab:

Calculate the amount of MTB-LAM-Ab solution necessary for conjugation to HRP. Place the MTB-LAM-Ab (from above) into a V-shaped glass vial with triangular stir bar, without leaving drops of the Ab solution on the vial walls. Add ½ volume of oxidized HRP solution (above) to the MTB-LAM-Ab solution, cover the vial with aluminum foil to protect reaction mixture from the light and stir reaction mixture in the glass vial for 30 min at room temperature. Avoid foaming.

Add 1 M Carbonate-HCl, to pH 9.5 and stir at room temperature for two hr. Protect from the light and avoid foaming.

Prepare 4 mg/ml Sodium Borohydride ($NaBH_4$) immediately before use and protect from the light with the aluminum foil. Immediately add the calculated amount of $NaBH_4$ required to the MTB-LAM-Ab solution prepared above, and incubate the reaction mixture at approx. 2-8° C. for 2 hr. Dialyze reaction mixture against 1×PBS for minimum 48 h at 2-8° C. with a minimum of 4 buffer changes at 8-16 hours intervals. Use 12-14 kDa cut-off dialyzing tubing for dialysis.

Conjugate Storage and Analysis:

After dialysis, centrifuge the conjugate solution at 4000 rpm for approx. 4 min. Carefully withdraw supernatant and place conjugate solution into the clean 6 ml glass vial. Measure 18 ml of Gardian Peroxidase Conjugate Stabilizer/Diluent into the 50 ml glass bottle with magnetic stir bar. Add 2 ml of MTB-LAM-Ab-HRP conjugate and stir the mixture for approx. 10 min. Store at 2-8° C., and protect from light.

The foregoing steps relating to MTB conjugate preparation are depicted schematically in FIG. 9.

Results

Below we present data from the evaluation of a direct antigen ELISA which detects LAM in unprocessed, non-concentrated urine using the "direct method" for enriched antibody production. (It is believed that even better data will result by using enriched antibodies produced using the "enhanced method" described above.) The studies producing these data were carried out in the Mbeya region that is located in the Southwestern highlands of Tanzania in collaboration with the Regional TB and Leprosy Programme and the Mbeya Medical Research Project (MMRP). In the Mbeya Region approximately 3,500 new TB cases are diagnosed annually and treatment is conducted according to the national DOTS strategy. Initiation of every therapy is initiated at a central facility at the Mbeya Referral Hospital. The TB cure rate was 72.3% in 2002. The aim of the study was to evaluate the performance of a commercially available LAM-capture ELISA in clinical practice and to compare the results with the gold standard for TB diagnosis:

Sputum microscopy, TB-culture, chest radiography and clinical investigation.

Material and Methods

LAM-ELISA Description

The MTB-ELISA direct antigen sandwich immunoassay (MTB-ELISA, Chemogen, So. Portland, Me., USA) is a LAM-ELISA similar to an assay developed by others. The immune sera were harvested from white New Zealand rabbits that were immunized with inactivated whole cells of *M tuberculosis* H37Rv. Polyclonal LAM-specific antibodies were isolated by affinity chromatography using immobilized LAM as a ligand. The test kit consists of an 96-well ELISA plate pre-coated with LAM-specific antibody, blocked and sealed in a plastic pouch with desiccant; a vial with LAM-specific HRP-conjugated LAM-specific polyclonal antibody; a vial with TMB (3,3',5,5'-tetramethylbenzidine) single component chromogenic substrate; a vial with the negative control solution, and three vials with calibrators corresponding to 0.5 ng/ml, 1.5 ng/ml and 4.5 ng/ml of LAM in urinary samples. Urine samples were considered positive in the ELISA when the obtained optical density at 450 nm was at least 0.1 above signal of the negative control (>2SD).

A patient urine sample of 0.1 ml is placed in duplicates on the ELISA plate, incubated for 1 hour and washed with 0.05% Tween-20/PBS (PBST) solution. 0.1 ml of LAM-specific HRP-conjugate are added. After 1 hour incubation the plate is washed with PBST solution and 0.1 ml of TMB substrate are added. After 10 minutes of incubation time the substrate reaction is stopped by adding 0.1 ml of 1M $H_2SO_4$ and the color development is read at 450 nm.

In other embodiments, the specific isoform of lipoarabinomannan (LAM) determined to contain the antigenic activity is used to generate highly specific, highly pure polyclonal antibodies for use in the detection of mycobacterium lipoarabinomannan in the urine of patients to be screened for active tuberculosis, using protocols similar to that described above. The antigenically active isoform of LAM was identified using selective oxidation of LAM, wherein two isoforms were readily identifiable and distinguishable (data not shown). One contained portions sensitive to high concentrations of sodium periodate ($NaIO_4$) such that at high concentrations of sodium periodate the serological activity of the LAM was destroyed. The other isoform maintained serological activity, even when subjected to high concentrations of sodium periodate. A comparison of two methods of oxidation of LAM, using either mild oxidizing agents or low concentrations of $NaIO_4$ preserved the antigenic activity of the LAM. Oxidation by high concentrations of $NaIO_4$, however, resulted in loss of antigenic activity of the LAM.

Therefore, only LAM activated with CNBr, or oxidized with mild oxidizing agents or low concentrations of $NaIO_4$ is used to generate highly antigenic LAM for use in the preparation of highly specific, highly pure polyclonal antibodies for use in detecting LAM in urine samples for diagnosing TB in patients of interest.

These results are completely unexpected compared to the detection methods disclosed by Svenson et al. (see e.g. WO97/34149) which used only high concentrations of $NaIO_4$ to oxidize the mycobacterial LAM, and consequently destroyed antigenic activity of the LAM used to generated the antibodies. Not knowing that there was more than one isoform of the LAM to be detected, it was not possible in the earlier disclosure to prepare highly specific antibodies to the antigenically active form of LAM, because no one prior to these studies even knew that a separate isoform existed that contained the antigenic activity, or that such activity was lost during standard means of oxidation, namely, treatment with high concentrations of $NaIO_4$.

Clinical Site Description.

Within eight weeks 242 suspected TB patients were recruited at the outpatient departments of 5 clinical centers in Mbeya, Tanzania. The standard protocol of investigation included clinical assessment, chest radiography, ESR, white blood cell×count and HIV test, 3×AFB staining (Ziehl Neelson) of sputum at day 1, 2 and 3, 2 sputum culture on Loewenstein Jenssen medium and LAM-ELISA in urine and serum.

All patients had clinical signs of TB (cough>4 weeks, night sweats, weight loss, loss of appetite). One hundred thirty-seven of these had laboratory confirmed pulmonary TB (PTB), 9 had high radiological suspicion of PTB (pleural effusions or enlarged hilar lymph nodes), and 8 showed clinical and radiological signs of military TB. Consenting patients were tested for their HIV status and 70% were confirmed as HIV-positive. Data were handled confidentially. The study was approved by the local Institutional review board and the national ethical committee of the Republic of Tanzania.

All laboratory procedures were performed in the laboratory facilities of the Mbeya Medical Research Project.

Microscopy and Culture of Sputum Samples

Ziehl Neelson staining and microscopy was done by an experienced and well qualified lab technician. After decontamination sputum samples were cultured on Loewenstein Jenssen medium in duplicates. Cultures were examined weekly for growth for 8 weeks.

Urine Specimens

From each patient 30 ml of urine were collected in a sterile plastic container, which was labeled with the code number of the respective patient's data form. 100l of fresh and unprocessed urine was added to the wells of the ELISA plate in duplicate. Negative controls, low, medium and high positive controls were also added to each plate in duplicates. Specimens were processed within 24 h and then stored at −20° C. for future testing in Germany.

Control Groups from Tanzania and USA

Urine samples of 23 staff members of the Mbeya Referral Hospital, of 20 staff members of Chemogen, Inc. and of 200 patients from 2 clinics in New York were tested in the LAM ELISA. All of them appeared healthy in clinical examination and did not have any signs of respiratory infections.

Results

Preclinical Evaluation of the ELISA System.

FIG. 4A shows the dose response curve using different concentrations of LAM in urine, wherein solid circles represent ELISA results using LAM from *M. tuberculosis*, and open circles represent the control ELISA results. The optimal cut off value was defined according to this curve as LAM concentration producing an optical density (OD) exceeding OD of negative control by 0.1 OD, that corresponds to more than 2 standard deviations above the signal of the negative control sample. All samples with an optical density above this cut off were considered as ELISA positive. The cut off was equal to approximately 0.25 ng/ml of LAM in untreated fresh urine.

The MTB-ELISA was evaluated for cross-reactivity with other species and genera of various Gram-positive and Gram-negative bacteria typical for urinary tract infections and bacterial pneumonia. None of the tested species has shown any reactivity in the evaluated LAM-ELISA system even at the highest tested concentrations, as can be seen by comparing the ELISA results for *M. tuberculosis* (open triangles) with the ELISA results for other bacterial species tested (solid triangles, open and solid diamonds, open and solid circles) depicted in FIG. 4B. An analysis of whole cells of various species of mycobacteria in the LAM-ELISA system shows cross-reactivity with all tested species of mycobacteria (M.) (FIG. 4C), however, *M. tuberculosis* H37Rv and *M. bovis* are detected most sensitively. Both species are very close from the immunochemical standpoint, but *M. bovis* is rarely a cause of mycobacterial infection in humans.

Study Participant Data

According to Table 1 the 242 TB suspects were divided into 3 major categories: (1) pulmonary TB patients with confirmed microscopic and/or culture diagnosis, (2) patients with typical clinical and radiographic signs and (3) patients with clinical symptoms of TB, that were not considered TB patients as all available diagnostic tools (radiography, sputum microscopy and culture) were negative.

Group one included 137 patients that had a laboratory confirmed pulmonary TB. 132 were confirmed by Loewenstein Jenssen culture and five had a negative culture but positive AFB-stain. Out of the 132 culture positive cases 62.12% were AFB positive.

Group two comprised an additional 17 patients that were enrolled into the DOTS therapy program based on radiographic and clinical findings (Table 1). The 88 patients of group three were sputum negative and did not present specific radiological signs of pulmonary TB and were therefore not enrolled in the DOTS program.

The mean age of the participants was 34 years. The female male ratio was 41:59. The overall HIV prevalence among the 223 patients that agreed to be tested for HIV was 69.1% (see Table 2). The HIV prevalence was 73.2% among patients with and 60.8% among patients without confirmed TB.

Clinical Evaluation of the ELISA

Of the 137 patients with confirmed pulmonary TB (culture or AFB positive) 111 were LAM-ELISA positive (sensitivity 81.02%) for the predefined cut off (optical density (OD) of negative control+0.1). The mean OD increment (=absolute mean OD–OD of negative control) for the smear and culture positive group (82) was 0.604. For smear negative and culture positive cases (50) the mean OD increment was 0.293 and for smear positive, but culture negative cases (5) 0.249.

Of the 17 patients in group two that were culture and AFB negative, but had typical radiological and clinical signs for TB 13 (76.47%) had a positive LAM-ELISA test results with a mean OD increment of 0.183. 13 (76.47%) of them were HIV positive.

The remaining 88 patients that came to the special TB clinic with clinical signs suggestive of pulmonary TB were culture and AFB negative and had no specific radiographic findings for TB. Of these 13 (14.77%) had a positive LAM-ELISA test (mean OD increment 0.184).

Based on the known concentration in the low, medium and high positive control that were included on each plate, it was possible to determine the approximate LAM concentration of each urine sample based on the OD value of the ELISA. Whether the LAM concentration correlates to the individual burden of tubercle bacteria was assessed in AFB positive patients. While patients with a low density of tubercle bacteria in microscopy (AFB+) had a mean LAM antigen concentration of 0.93 ng/ml in the urine, patients with an intermediate density of acid fast bacilli (AFB++) had a mean antigen concentration of 1.74 ng/ml in their urine and AFB+++patients 2.02 ng/ml (FIG. 5). The later value is lower than the real concentration of LAM in urine of AFB+++patients because the ELISA reader used in the Tanzania lab could not read signals above two corresponding to about 4 ng/ml.

The HIV serostatus did not influence the sensitivity of the LAM-ELISA in confirmed pulmonary TB patients. Of 124 patients with known HIV serostatus and positive TB culture and/or AFB stain 73 of 89 HIV infected patients (82.0%) were positive in the LAM-ELISA compared to 26 out of 35 uninfected individuals (74.3%). Similarly, the sensitivity of the AFB was not compromised by HIV serostatus. The sensitivity was 61.2% and 58.8% in HIV infected and negative individuals, respectively.

The specificity of the assay was assessed using the urine of healthy Tanzanian and US volunteers. The urine of 23 healthy hospital staff members of Tanzanian origin was analyzed. None of the samples was tested positive in LAM-ELISA (−0.047 mean relative OD, specificity 100%). Urine samples of 220 healthy volunteers from US were collected and analyzed. All but 4 had an optical density below the cut off 0.1 (specificity 98.18%).

Discussion

The classical tools for the diagnosis of TB, sputum culture and smear microscopy, have obvious limitations. Both methods only detect cases of open pulmonary TB. This significantly impairs the possibility of the detection of all cases of active TB regardless of the organ manifestation. Therefore multiple new methods have been evaluated in the past that could supplement the classic tools, especially in resource poor settings. The criteria that were set for such a new assay are a) a higher sensitivity than microscopy, b) comparable specificity, c) a limited additional work load, d) the possibility to diagnose sputum-negative TB and e) a sensitivity that is not impaired by HIV co-infection.

In this first evaluation, the sensitivity of the LAM-ELISA (81% of culture positives) was superior to AFB-stain (69%). Sensitivity can be further improved by concentrating fresh urine, which would however result in an additional effort for a lab technician. The detection rate of the LAM-ELISA for cases with radiological confirmed military TB.(87.5%) as well as for sputum negative cases with typical radiological signs of pulmonary TB (67%) was encouraging, although the case numbers were not high enough to allow a final conclusion. For healthy individuals the specificity of the ELISA was high (98.18% in US and 100% in Tanzania). HIV co-infection in culture positive TB cases did not influence the sensitivity of the LAM-ELISA.

In comparison to previous published results of the LAM-ELISA the new test detects LAM at lower concentrations (0.2 ng/ml) than former tests. The sensitivity of the new test was 82.9% (of AFB+) for unconcentrated and fresh urine compared to a sensitivity of 81.3% for the previous test using processed and frozen urine. The test specificity was 98.36% in this study compared to 86.9% in the previous study.

The limitation of this cross sectional TB study was the fact that a certain proportion of TB suspected patients remained ambiguous in terms of their TB status (group 2 and 3). To acknowledge this problem we have created three major categories for analysis: Group 1: laboratory confirmed TB, Group 2: clinically and radiological diagnosed TB, Group 3: no laboratory or radiological proof of TB. While we are confident that participants in category I are true TB cases, we cannot exclude that category 2 and 3 contain some wrongly categorized patients. We therefore excluded them from our sensitivity and specificity calculation. Diagnosis of TB often requires the longitudinal follow-up of patients. Especially sputum negative patients with unusual radiological features would have needed several follow-up consultations in order to re-question their TB status. In a longitudinal study clinical as well as diagnostic reevaluation and TB treatment outcome would have given important additional information to classify group 2 and 3 in TB and non TB patients.

Of major interest is the question if there is a quantitative correlation between the bacterial burden of *M. tuberculosis* and the amount of LAM detected in urine. The only way to address this question in a cross sectional study format was to correlate the AFB sputum staining score with concentration of LAM in urine. As shown in FIG. 5 there was an obvious positive correlation of antigen concentration in urine and tubercle bacteria density in sputum. Such a correlation opens up several additional applications for the LAM assay. The monitoring of treatment success and the early recognition of relapses after completion of treatment are of immediate practical relevance. The combination of a sensitive urine assay with the capacity to detect extrapulmonary and AFB-negative TB renders the LAM assay a potent tool in an environment with a growing prevalence of extrapulmonary forms of TB and pulmonary forms with atypical clinical symptoms. The LAM-ELISA could not only be used for the diagnosis of patients with clinical symptoms, but also for screening HIV positive patients and other high risk groups. Early case detection of active TB and effective treatment are the two pillars in a successful fight against TB. To further explore the role of the LAM assay in this fight we are currently planning several prospective and multicenter studies.

In summary, the LAM-ELISA can be easily integrated in the routine diagnostic procedures of laboratories of both, developed and developing countries. It is an easy to use and robust assay. Completion of the ELISA requires only 2 hr and many samples can be analyzed at the same time. As the antigen Lipoarabinomannan is stable, it was possible to keep the urine refrigerated for 3 days without significant drop in optical density. The newly developed MTB-ELISA for detection of LAM in unprocessed urine has the potential of a screening test to be used also under field conditions in developing countries.

What is claimed is:

1. A method for detecting a mycobacterial infection in a sample from a subject of interest by detecting mycobacterial antigen in the sample, the method comprising:

providing an immunoreactive environment comprising the sample and an immunoassay, such immunoassay using a polyclonal antibody highly specific for the mycobacterial antigen, the antigen being a surface polysaccharide from a mycobacterium, wherein the surface polysaccharide is lipoarabinomann (LAM) and the polyclonal antibody is enriched by exclusion of antibodies that recognize antigen modified by oxidation with $NaIO_4$; and reacting the sample with the immunoassay in the immunoreactive environment to detect mycobacterial antigen in the sample, so as to detect the mycobacterial infection, wherein an immunoassay result which is elevated compared to a negative control is considered positive for a mycobacterial infection.

2. A method according to claim 1, wherein the mycobacterial infection is *M. tuberculosis*.

3. A method according to claim 1, wherein the immunoassay comprises an enzyme-linked immunosorbent assay.

4. A method according to claim 1, wherein the mycobacterial infection is Johne's disease.

TABLE 1

Analysis of urinary LAM excretion in the 242 patients coming to the OPD with clinical suspicion for TB and the 243 clinically healthy controls. The cut off value for LAM-ELISA positivity is 0.1 above the mean optical density of the negative control on the plate. + = positive.

| Study Group | TB Diagnosis | Participants | LAM+ | LAM− |
|---|---|---|---|---|
| 1: Laboratory Confirmed TB | LJ+ and/or AFB | 137 | 111 (81.02%) | 26 |
| | LJ+ and AFB+ | 82 | 68 (82.9%) | 14 (17.1%) |
| | Only LJ+ | 50 | 38 (76%) | 12 (24%) |
| | Only AFB+ | 5 | 5 (100%) | 0 (0%) |
| 2: Clinically and Radiologically diagnosed TB | Military TB | 8 | 7 (87.5%) | 1 (12.5%) |
| | Pleural effusion or enlarged hilar lymph | 9 | 6 (67%) | 3 (33%) |
| 3: No laboratory or radiological proof of TB | Only clinical signs of TB. No enrollment in DOTS | 88 | 13 (14.77%) | 75 (85.23%) |
| 4: Negative Control Group | No clinical signs of TB | 243 | 4 (1.64%) | 239 (98.36%) |

TABLE 2

Proportion of HIV positive patients in the different groups. 223 of 242 patients consented to be tested for HIV.

| | HIV+ |
|---|---|
| All TB suspects | 69.1% |
| Culture+ (119) | 71.% |
| AFB+ (77) | 72.7% |
| EXPTB (17) | 76.47% |

5. A method according to claim 1, wherein the mycobacterial infection is a pulmonary *Mycobacterium tuberculosis* infection.

6. A method according to claim 1, wherein the mycobacterial infection is an extra-pulmonary *Mycobacterium tuberculosis* infection.

7. A method according to claim 1, wherein the sample is any of sputum, blood, urine, tissue or other suitable sample.

8. A method according to claim 1, wherein the sample is non-processed unconcentrated uring.

* * * * *

UNITED STATES PATENT AND TRADEMARK OFFICE
CERTIFICATE OF CORRECTION

PATENT NO. : 7,335,480 B2
APPLICATION NO. : 11/186933
DATED : February 26, 2008
INVENTOR(S) : Vladimir A. Koulchin et al.

It is certified that error appears in the above-identified patent and that said Letters Patent is hereby corrected as shown below:

Col. 24, line 10
replace "surface polysaccharide is lipoarabinomann"
with --surface polysaccharide is lipoarabinomannan--

Signed and Sealed this

Twentieth Day of May, 2008

JON W. DUDAS
*Director of the United States Patent and Trademark Office*